(12) United States Patent
Snyder et al.

(10) Patent No.: US 10,688,096 B2
(45) Date of Patent: Jun. 23, 2020

(54) METHODS FOR TREATMENT OF SLEEP-RELATED BREATHING DISORDERS

(75) Inventors: Solomon H. Snyder, Baltimore, MD (US); Moataz M. Gadalla, Baltimore, MD (US); Nanduri R. Prabhakar, Chicago, IL (US); Gregory Stein, San Diego, CA (US); Gary Pace, La Jolla, CA (US)

(73) Assignees: The University of Chicago, Chicago, IL (US); The Johns Hopkins University, Baltimore, MD (US)

( * ) Notice: Subject to any disclaimer, the term of this patent is extended or adjusted under 35 U.S.C. 154(b) by 422 days.

(21) Appl. No.: 13/640,711

(22) PCT Filed: Apr. 11, 2011

(86) PCT No.: PCT/US2011/031977
§ 371 (c)(1),
(2), (4) Date: Feb. 1, 2013

(87) PCT Pub. No.: WO2011/130181
PCT Pub. Date: Oct. 20, 2011

(65) Prior Publication Data
US 2013/0131028 A1 May 23, 2013

Related U.S. Application Data

(60) Provisional application No. 61/347,069, filed on May 21, 2010, provisional application No. 61/323,621, filed on Apr. 13, 2010.

(51) Int. Cl.
*A61K 31/198* (2006.01)
*A61K 31/519* (2006.01)
(Continued)

(52) U.S. Cl.
CPC .......... *A61K 31/519* (2013.01); *A61K 31/165* (2013.01); *A61K 31/198* (2013.01);
(Continued)

(58) Field of Classification Search
None
See application file for complete search history.

(56) References Cited

U.S. PATENT DOCUMENTS 4,229,447 A 10/1980 Porter
4,596,795 A 6/1986 Pitha
(Continued)

FOREIGN PATENT DOCUMENTS

WO  WO 2010/010383 A1  1/2010
WO  WO 2010010383 A1 * 1/2010
(Continued)

OTHER PUBLICATIONS

Eckert et al., "Central Sleep Apnea: Pathophysiology and Treatment," Chest Feb. 2007; 131(2):595-607.*
(Continued)

*Primary Examiner* — Timothy P Thomas
(74) *Attorney, Agent, or Firm* — Norton Rose Fulbright US LLP

(57) ABSTRACT

Described herein are methods for modulation of the activity of the carotid body that afford therapeutic benefit for sleep-related breathing disorders and related conditions.

9 Claims, 14 Drawing Sheets

(51) Int. Cl.

| | | |
|---|---|---|
| *A61K 31/385* | (2006.01) | |
| *A61K 31/4178* | (2006.01) | |
| *A61K 45/06* | (2006.01) | |
| *A61K 31/409* | (2006.01) | |
| *A61K 31/165* | (2006.01) | |
| *A61K 31/24* | (2006.01) | |
| *A61K 31/28* | (2006.01) | |
| *A61K 31/404* | (2006.01) | |
| *A61K 31/4164* | (2006.01) | |

(52) U.S. Cl.
CPC .............. *A61K 31/24* (2013.01); *A61K 31/28* (2013.01); *A61K 31/385* (2013.01); *A61K 31/404* (2013.01); *A61K 31/409* (2013.01); *A61K 31/4164* (2013.01); *A61K 31/4178* (2013.01); *A61K 45/06* (2013.01)

(56) References Cited

U.S. PATENT DOCUMENTS

| | | |
|---|---|---|
| 4,755,386 A | 7/1988 | Hsiao et al. |
| 5,739,136 A | 4/1998 | Ellinwood, Jr. et al. |
| 6,331,536 B1 | 12/2001 | Radulovacki et al. |
| 2009/0214673 A1* | 8/2009 | Ohia et al. .................... 424/708 |

FOREIGN PATENT DOCUMENTS

| | | | | |
|---|---|---|---|---|
| WO | WO 2011/130181 A1 | | 10/2011 | |
| WO | WO 2011130181 A1 * | | 10/2011 | ........... A61K 31/165 |

OTHER PUBLICATIONS

Supuran et al., "Carbonic anhydrase inhibitors as emerging drugs for the treatment of obesity," Expert Opin Emerg Drugs, Jun. 2008;13(2):383-92.*
Schwartz et al., "Obesity and Obstructive Sleep Apnea Pathogenic Mechanisms and Therapeutic Approaches," Proceedings of the American Thoracic Society, vol. 8, 2008, pp. 185-192.*
Zhang et al.; "Serum level of endogenous hydrogen sulfide in patients with obstructive sleep apnea hypopnea syndrome"; 2009; Zhongguo Shiyong Neike Zazhi; 29(11): 1049-1050; SciFinder abstract; Accession Number: 2009:1621936.*
Olsen et al.; Hypoxic pulmonary vasodilation: a paradigm shift with a hydrogen sulfide mechanism; 2010; Am. J. Physiol. Regu I. Integr. Comp. Physiol.; 298: R51-R60.*
Sun et al.; "Structural Basis for the Inhibition Mechanism of Human Cystathionine γ-Lyase, an Enzyme Responsible for the Production of H2S"; 2009; The Journal of Biological Chemistry; 284(5): 3076-3085.*
Javaheri; "Acetazolamide Improves Central Sleep Apnea in Heart Failure"; 2006; American Journal of Respiratory and Critical Care Medicine; 173(2): 234-237.*
Livertox; Carbonic Anhydrase Inhibitor Diuretics; https://livertox.nlm.nih.gov/CarbonicAnhydraseInhibitorDiuretics.htm; accessed Oct. 19, 2016.*
Cho et al.; "Propargylglycine infusion effects on tissue glutathione levels, plasma amino acid concentrations and tissue morphology in parenterally-fed growing rats"; 1991; The Journal of nutrition; 121(6): 785-94; SciFinder abstract; Accession No. 1991237445.*
Dictionary.com; "Analogue"; http://www.dictionary.com/browse/analog; accessed Oct. 19, 2016.*
Merriam-Webster; "Derivative"; http://www.merriam-webster.com/dictionary/derivative; accessed Oct. 19, 2016.*
Abeles et al. Acetylenic enzyme inactivators. Inactivation of gamma-cystathionase, in vitro and in vivo, by propargylglycine. J Am Chem Soc. Sep. 5, 1973;95(18):6124-6125.
CA2796268 Office Action dated Jun. 7, 2013.
Caliendo et al. Synthesis and biological effects of hydrogen sulfide (H2S): development of H2S-releasing drugs as pharmaceuticals. J Med Chem. Sep. 9, 2010;53(17):6275-6286.
EP11769384.6 Extended European Search Report dated Jul. 2, 2013.
Kinobe et al. Effectiveness of novel imidazole-dioxolane heme oxygenase inhibitors in renal proximal tubule epithelial cells. J Pharmacol Exp Ther. Dec. 2003;323(3):763-770.
Kinobe et al. Inhibitors of the heme oxygenase—carbon monoxide system: on the doorstep of the clinic? Can J Physiol Pharmacol. Sep. 2008;86(9):577-599.
Li et al. A crucial role for hydrogen sulfide in oxygen sensing via modulating large conductance calcium-activated potassium channels. Antioxidants & Redox Signaling. May 15, 2010; 12(10): 1179-1189.
Muzaffar et al., "H2S-donating sildenafil (ACS6) inhibits superoxide formation and gpp1phox expression in arterial endothelial cells: role of protein kinases A and G", British Journal of Pharmacology (2008) 155, 984-994.
NZ603553 Office Action dated Jun. 7, 2013.
PCT/US2011/31977 International preliminary report on patentability dated Oct. 16, 2012.
PCT/US2011/31977 International search report dated Jul. 5, 2011.
PCT/US2011/31977 Written opinion of the International Searching Authority dated Jul. 5, 2011.
Wallace et al. Markedly reduced toxicity of a hydrogen sulphide-releasing derivative of naproxen (ATB-346). Br J Pharmacol. Mar. 2010;159(6):1236-1246.
Washtein et al. Mechanism of inactivation of gamma-cystathionase by the acetylenic substrate analogue propargylglycine. Biochemistry. May 31, 1977;16(11):2485-2491.

\* cited by examiner

FIGURE 7

|  | CSE $^{+/+}$ (n=8) | | CSE $^{+/-}$ (n=8) | |
|---|---|---|---|---|
|  | 21% O$_2$ | 12% O$_2$ | 21% O$_2$ | 12% O$_2$ |
| RR(breaths/min) | 174±2 | 231±3 | 140±5** | 175±5** |
| V$_T$(μl/g) | 2.31±0.10 | 2.65±0.06 | 2.14±0.09 $^{n.s.}$ | 2.44±0.12 $^{n.s.}$ |
| V$_E$(ml/g·min) | 0.40±0.02 | 0.61±0.02 | 0.30±0.02** | 0.43±0.03** |
| VO$_2$(ml/g·min) | 0.05±0.003 | 0.03±0.002 | 0.05±0.002 $^{n.s.}$ | 0.03±0.003 $^{n.s.}$ |
| VCO$_2$(ml/g·min) | 0.04±0.002 | 0.02±0.002 | 0.04±0.003 $^{n.s.}$ | 0.02±0.001 $^{n.s.}$ |
| V$_E$/VO$_2$ | 7.7±0.38 | 22.1±1.90 | 6.5±0.8 $^{n.s.}$ | 16.4±2.22* |

FIGURE 8

|  | CSE $^{+/+}$ (n=8) | | CSE $^{-/-}$ (n=8) | |
| --- | --- | --- | --- | --- |
|  | 21%O$_2$ | 5% CO$_2$ | 21%O$_2$ | 5% CO$_2$ |
| RR(breaths/min) | 167±4 | 273±13.8 | 140±5* | 238±13 n.s. |
| V$_T$(μl/g) | 2.36±0.12 | 3.23±0.21 | 2.13±0.15 n.s. | 3.81±0.27 n.s. |
| V$_E$(ml/g·min) | 0.39±0.03 | 0.89±0.10 | 0.30±0.03* | 0.92±0.10 n.s. |

METHODS FOR TREATMENT OF SLEEP-RELATED BREATHING DISORDERS

CROSS-REFERENCE

This application is filed pursuant to 35 U.S.C. § 371 as a United States National Phase Application of International Application No. PCT/US2011/031977, filed Apr. 11, 2011, which claims the benefit of U.S. Provisional Application No. 61/323,621 filed Apr. 13, 2010; and U.S. Provisional Application No. 61/347,069 filed May 21, 2010; each of which is incorporated herein by reference in its entirety.

STATEMENT AS TO FEDERALLY SPONSORED RESEARCH

This invention was made with government support under grant nos. HL076537, HL090554, HL086493, DA000226, DA000074, and GM007309 awarded by the National Institutes of Health. The government has certain rights in the invention.

BACKGROUND OF THE INVENTION

The carotid body is a sensory organ that monitors oxygen ($O_2$) levels and/or carbon dioxide levels ($CO_2$) in arterial blood and regulates breathing.

SUMMARY OF THE INVENTION

Described herein are methods for modulating the activity of the carotid body. In some embodiments, the methods described herein allow for modulation of chemosensitivity of the carotid body in response to hypoxia. In some embodiments, alteration of the response of the carotid body to certain gasotransmitters including and not limited to hydrogen sulfide ($H_2S$), and/or carbon monoxide (CO), allows for treatment of sleep-related breathing disorders. In some embodiments, modulation of the sensory response of the carotid body reduces the activity of the carotid body in individuals in need thereof. In other embodiments, modulation of the sensory response of the carotid body increases the activity of the carotid body in individuals in need thereof.

In mammals, the carotid body comprises peripheral chemoreceptors that are associated with control of ventilation in response to oxygen levels in blood. The carotid body is linked to the central chemoreceptors in the brainstem and relays sensory information to brainstem neurons that are associated with regulation of breathing and/or the cardiovascular system. Accordingly, further provided herein are methods of treatment of diseases or conditions that are associated with carotid body activity and/or control of ventilation in individuals in need thereof.

Provided herein, in some embodiments, are methods of treating or preventing or reducing the incidence of sleep-related breathing disorders in individuals in need thereof comprising administration of a therapeutically effective amount of an agent that modulates the activity of the carotid body to the individual in need thereof. In some of such embodiments, the individual is suffering from or suspected to be suffering from a sleep-related breathing disorder selected from central sleep apnea (CSA), Cheyne-Stokes breathing-central sleep apnea (CSB-CSA), obesity hypoventilation syndrome (OHS), congenital central hypoventilation syndrome (CCHS), obstructive sleep apnea (OSA), idiopathic central sleep apnea (ICSA), narcotic-induced CSA (including opioid-induced central sleep apnea), high altitude periodic breathing, chronic mountain sickness, impaired respiratory motor control associated with stroke, or impaired respiratory motor control associated with a neurologic disorder.

In some specific embodiments, the individual is suffering from or suspected to be suffering from central sleep apnea (CSA). In some specific embodiments, the individual is suffering from or suspected to be suffering from Cheyne-Stokes breathing-central sleep apnea (CSB-CSA). In some specific embodiments, the individual is suffering from or suspected to be suffering from obesity hypoventilation syndrome (OHS). In some specific embodiments, the individual is suffering from or suspected to be suffering from congenital central hypoventilation syndrome (CCHS). In some specific embodiments, the individual is suffering from or suspected to be suffering from obstructive sleep apnea (OSA). In some specific embodiments, the individual is suffering from or suspected to be suffering from idiopathic central sleep apnea (ICSA). In some specific embodiments, the individual is suffering from or suspected to be suffering from opioid-induced CSA. In some specific embodiments, the individual is suffering from or suspected to be suffering from high altitude periodic breathing. In some specific embodiments, the individual is suffering from or suspected to be suffering from chronic mountain sickness. In some specific embodiments, the individual is suffering from or suspected to be suffering from impaired respiratory motor control associated with stroke. In some specific embodiments, the individual is suffering from or suspected to be suffering from impaired respiratory motor control associated with a neurologic disorder.

In some of the aforementioned embodiments, the agent that modulates the activity of the carotid body is an agent that inhibits or partially inhibits the activity of cystathionine-gamma-lyase (CSE). In some embodiments, the agent that inhibits or partially inhibits the activity of CSE reduces the chemosensitivity of the carotid body to the partial pressure of oxygen in arterial blood, reduces the chemosensitivity of the carotid body to the partial pressure of carbon dioxide in arterial blood, reduces the loop gain of the ventilatory drive control system, lowers blood pressure, or dampens carotid sinus nerve activity in an individual in need thereof, or a combination thereof.

In some specific embodiments, the agent that inhibits or partially inhibits the activity of CSE reduces the chemosensitivity of the carotid body in an individual in need thereof. In some embodiments, the agent that inhibits or partially inhibits the activity of CSE reduces the chemosensitivity of the carotid body to the partial pressure of oxygen in arterial blood. In some embodiments, the agent that inhibits or partially inhibits the activity of CSE reduces the loop gain of the ventilatory drive control system in an individual in need thereof. In some embodiments, the agent that inhibits or partially inhibits the activity of CSE reduces blood pressure in an individual in need thereof. In some embodiments, the agent that inhibits or partially inhibits the activity of CSE dampens carotid sinus nerve activity. In some embodiments, the agent that inhibits or partially inhibits the activity of CSE is DL-propargylglycine (PAG), beta cyano alanine (BCA), or analog or derivative thereof.

In some embodiments, the agent that modulates the activity of the carotid body is an agent that inhibits or partially inhibits hemeoxygenase-2 enzyme (HO-2), or is an $H_2S$ donor. In some embodiments, the agent that inhibits or partially inhibits hemeoxygenase-2 enzyme is an agent that stimulates the chemosensitivity of the carotid body in an individual in need thereof. In some embodiments, the agent that inhibits or partially inhibits hemeoxygenase-2 enzyme decreases production of carbon monoxide in the carotid body, increases production of H₂S in the carotid body, or increases carotid sinus nerve activity in an individual in need thereof.

In some embodiments, the agent that inhibits or partially inhibits hemeoxygenase-2 enzyme decreases production of carbon monoxide in the carotid body of an individual in need thereof. In some embodiments, the agent that inhibits or partially inhibits hemeoxygenase-2 enzyme increases production of H₂S in the carotid body of an individual in need thereof. In some embodiments, the agent that inhibits or partially inhibits hemeoxygenase-2 enzyme increases carotid sinus nerve activity. In some embodiments, the agent that inhibits or partially inhibits hemeoxygenase-2 enzyme is Cr(III) mesoporphyrin IX chloride, or analog or derivative thereof. In some embodiments, the agent that inhibits or partially inhibits hemeoxygenase-2 enzyme and modulates the activity of the carotid body is

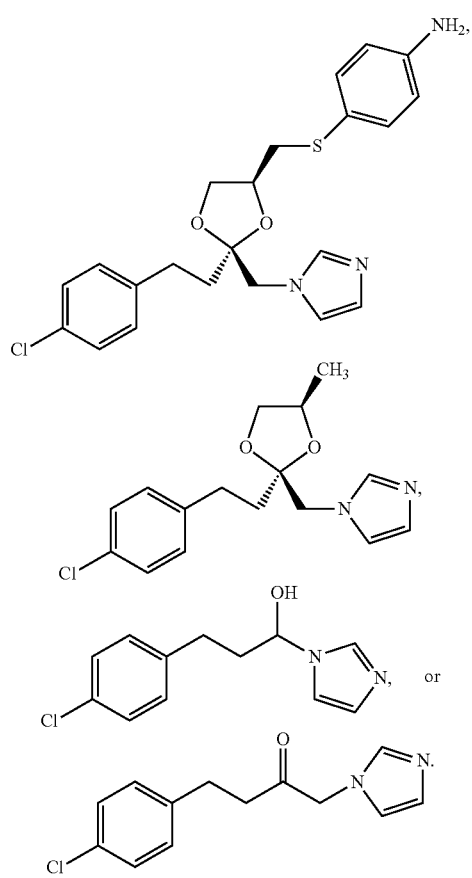

In some embodiments, an H₂S donor stimulates the chemosensitivity of the carotid body in an individual in need thereof. In some embodiments, an H₂S donor decreases production of carbon monoxide in the carotid body, increases concentration of H₂S in the carotid body, or increases carotid sinus nerve activity in an individual in need thereof.

In some embodiments, an H₂S donor, decreases production of carbon monoxide in the carotid body of an individual in need thereof. In some embodiments, In some embodiments, an H₂S donor increases carotid sinus nerve activity.

In some embodiments, the agent that is an H₂S donor and modulates the activity of the carotid body is

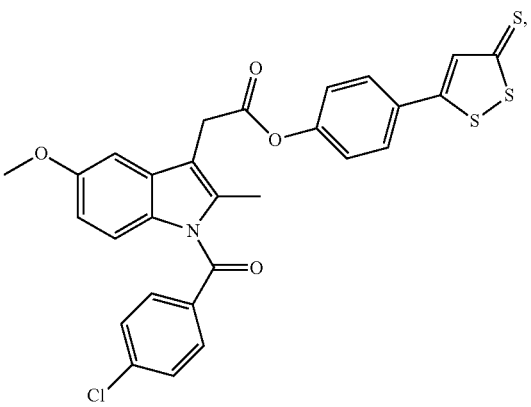

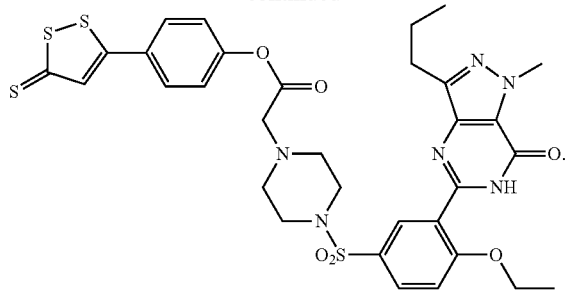 [SMILES: CCCc1nn(C)c2c(=O)[nH]c(-c3cc(S(=O)(=O)N4CCN(CC(=O)Oc5ccc(-c6cc(=S)ss6)cc5)CC4)ccc3OCC)nc12]

Also provided herein are methods of treatment of CSB-CSA comprising administering to an individual in need thereof a therapeutically effective amount of an agent that inhibits or partially inhibits CSE.

Further provided herein are methods of treatment of obesity hypoventilation syndrome (OHS) and/or other alveolar hypoventilation syndromes comprising administering to an individual in need thereof a therapeutically effective amount of an agent that inhibits or partially inhibits HO-2, or is an $H_2S$ donor.

In certain embodiments, the methods described above further comprise administration of a second agent selected from carbonic anhydrase inhibitors, cholinesterase inhibitors, adenosine inhibitors, progestational agents, opioid antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists.

In certain embodiments, the methods described above further comprise administration of a second agent selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, and sabeluzole.

In some embodiments of the methods described above, the agent that modulates the activity of the carotid body is administered orally, subcutaneously, topically, intramuscularly, or intravenously. In certain embodiments of the methods described above, the agent that modulates the activity of the carotid body is administered orally.

In one aspect, provided herein are single pill co-formulations comprising (i) an agent that modulates the activity of the carotid body and (ii) an agent selected from carbonic anhydrase inhibitors, cholinesterase inhibitors, adenosine inhibitors, progestational agents, opiod antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists.

In some of such embodiments, a single pill co-formulation comprises a CSE inhibitor and an agent selected from carbonic anhydrase inhibitors, cholinesterase inhibitors, adenosine inhibitors, progestational agents, opiod antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists.

In some of such embodiments, a single pill co-formulation comprises a hemeoxygenase-2 inhibitor and an agent selected from carbonic anhydrase inhibitors, cholinesterase inhibitors, adenosine inhibitors, progestational agents, opiod antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists.

In some of such embodiments, a single pill co-formulation comprises an $H_2S$ donor and an agent selected from carbonic anhydrase inhibitors, cholinesterase inhibitors, adenosine inhibitors, progestational agents, opiod antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists.

For single pill co-formulations described above, any combination of first agent and second agent is contemplated as being within the scope of embodiments presented herein.

In one aspect, provided herein are methods of identifying a CSE inhibitor comprising
(a) administration of a test compound to a test animal;
(b) preparing carotid body homogenates from the test animal;
(c) determining $H_2S$ concentration in the homogenate;
wherein a decrease in $H_2S$ concentration indicates that the test compound is a CSE inhibitor.

In another aspect, provided herein are methods of identifying a CSE inhibitor comprising
(a) administration of a test compound to a test animal;
(b) isolating carotid bodies along with carotid sinus nerves from the test animal;
(c) challenging the carotid bodies with varying levels of oxygen and carbon dioxide; and
(d) recording action potentials of the nerve bundles;
wherein a decrease in action potential indicates that the test compound is a CSE inhibitor.

In yet another aspect, provided herein are methods of identifying a HO-2 inhibitor comprising
(a) administration of a test compound to a test animal;
(b) isolating carotid bodies along with carotid sinus nerves from the test animal;
(c) challenging the carotid bodies with varying levels of oxygen and carbon dioxide; and
(d) recording action potentials of the nerve bundles;
wherein an increase in action potential indicates that the test compound is a HO-2 inhibitor.

Provided herein is the use of an agent that modulates the activity of the carotid body in the manufacture of a medicament for treating or preventing sleep-related breathing disorders in individuals in need thereof comprising administration of a therapeutically effective amount of an agent that modulates the activity of the carotid body to the individual in need thereof.

INCORPORATION BY REFERENCE

All publications, patents, and patent applications mentioned in this specification are herein incorporated by reference in support of and for the purposes cited herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7. Illustrates hypoxic ventilatory responses in $CSE^{+/+}$ and $CSE^{-/-}$ mice. Respiratory rate (RR), tidal volume ($V_T$), and $V_E$ (RR×$V_T$) were determined by whole body plethysmography in unsedated mice. $O_2$ consumption ($V_{O2}$) and carbon dioxide production (Vco2) were determined as described in methods. Results are presented as mean± SEM. ** denote p<0.01 compared to CSE mice. n.s. denotes p>0.05; not significant. n represents number of mice.

FIG. 8. Illustrates Hypercapnic ventilatory responses in $CSE^{+/+}$ and $CSE^{-/-}$ mice. RR (Respiratory rate), $V_T$ tidal volume, and $V_E$ (RR×$V_T$). Results are presented as mean±SEM. ** denote p<0.01 compared to CSE+/÷ mice. n.s. denotes p>0.05; not significant. n represents number of mice.

DETAILED DESCRIPTION OF THE INVENTION

Figure 1:
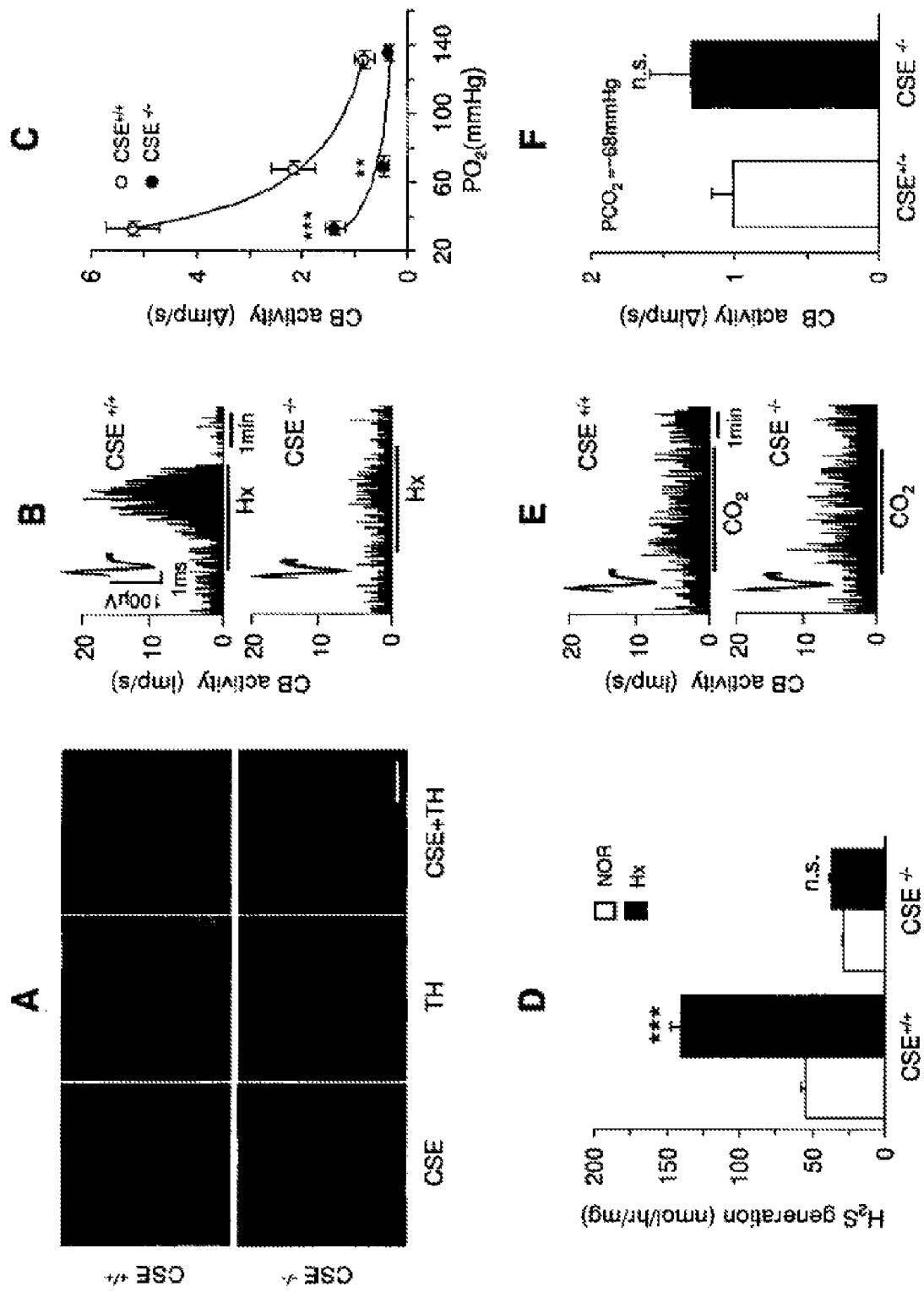
FIG. 1. (A). Illustrates cystathionine γ-lyase (CSE) expression in carotid bodies from $CSE^{+/+}$ and $CSE^{-/-}$ mice. Carotid body sections were stained with antibodies specific for CSE or tyrosine hydroxylase (TH), a marker of glomus cells. Horizontal bar represents 20 gm. (B). Sensory response of isolated carotid bodies to hypoxia (Hx; $P_{O2}$, ~39 mmHg; at black bar) in $CSE^{+/+}$ and $CSE^{-/-}$ mice. Integrated carotid body sensory activity (CB activity) is presented as impulses per second (imp/s). Superimposed action potentials from the single fiber are presented in the inset. (C). Carotid body responses to graded hypoxia from $CSE^{+/+}$ $CSE^{-/-}$ mice, measured as the difference in response between baseline and hypoxia (Δimp/s). Data is mean±SEM of n=24 ($CSE^{+/+}$) and n=23 ($CSE^{-/-}$) fibers from 8 mice each. (D). $H_2S$ levels (mean±SEM) in carotid bodies from $CSE^{+/+}$ and $CSE^{-/-}$ mice under normoxia (NOR) and hypoxia (Hx; $P_{O2}$, ~40 mmHg) from 4 independent experiments. (E) Example illustrating carotid body responses to $CO_2$ ($P_{CO2}$~68 mmHg; at black bar) in $CSE^{+/+}$ and $CSE^{-/-}$ mice. (F) Average data (mean±SEM) of $CO_2$ response from n=24 ($CSE^{+/+}$) and n=19 ($CSE^{-/-}$) fibers from 8 mice in each group. * and  represent p<0.001 and p<0.01, respectively. n.s. represent p>0.05 i.e. not significant.

Provided herein are methods for modulating the activity of the carotid body in an individual. Also provided herein are methods for modulating gasotransmitter pathways associated with regulation of breathing. Gaseous messengers such as hydrogen sulfide, and carbon monoxide, play a role in oxygen sensing by the carotid body. Reflexes arising from the carotid body have been implicated in pathological situations including and not limited to sleep-related breathing disorders (SRBD) with recurrent apnea (i.e., periodic cessations of breathing) and/or hypoapnea (i.e., reduced breath amplitude). Patients with recurrent apnea experience periodic hypoxemia and/or intermittent hypoxia and are prone to autonomic morbidities including, for example, hypertension. SRBD includes a range of conditions that manifest pathologically as central apnea, obstructive apnea or mixed apnea.

Current therapy for sleep-related breathing disorders utilizes mechanical devices to aid breathing. Such assisted breathing and/or alleviation of apnea includes application of positive airway pressure to an individual in need thereof. The mode of application of positive airway pressure depends on whether the apneas are caused by hyperventilation or hypoventilation. Continuous positive airway pressure (CPAP) is suitable for patients whose central apneas are due to hyperventilation. CPAP reduces the frequency of apneas by preventing pharyngeal airway narrowing and occlusion during sleep. Another therapeutic approach involves the use of noninvasive positive pressure ventilation (NIPPV), such as pressure support ventilation (PSV) or bilevel positive airway pressure (BiPAP), with a set backup respiratory rate. However, in some instances, BiPAP without a backup respiratory rate exacerbates hyperventilation, hypocapnia, and central apnea by augmenting tidal volume. NIPPV potentially worsens alveolar ventilation. Adaptive servo-ventilation (ASV) provides a small but varying amount of inspiratory pressure superimposed on a low level of CPAP. The magnitude of the inspiratory pressure is reciprocal to the amount of respiratory effort. Supplemental oxygen and/or supplemental carbon dioxide are also used in current therapy under tightly controlled delivery. Current pharmacologic therapy includes the use of respiratory stimulants. However, none of these therapeutic approaches address the underlying pathology of sleep-related breathing disorders.

Described herein are therapeutic approaches for the treatment of sleep-related breathing disorders. In some embodiments, such methods allow for modulation of the activity of the carotid body, an organ involved in hypoxic sensing and control of breathing.

Carotid Body

In adult mammals, carotid bodies are peripheral sensory organs responsible for monitoring arterial blood $CO_2$ and/or $O_2$ concentrations and relaying sensory information to the brainstem neurons associated with regulation of breathing and the cardiovascular system. The carotid body (carotid glomus or glomus caroticum) is a highly vascularized region located near the bifurcation of the carotid artery and comprises a cluster of peripheral chemoreceptors and supporting cells. The carotid body is linked to the central chemoreceptors found in the brainstem; interaction of the peripheral and central chemoreceptors controls ventilation in mammals. Carotid bodies are the primary mediators of ventilatory stimulation induced under conditions of acute hypoxia.

Carotid bodies comprise two cell types: glomus (also called type I) and sustanticular (or type II) cells. Glomus cells, of neuronal nature, are hypoxia sensing cells. The gaseous messenger, carbon monoxide (CO), generated by hemeoxygenase II (HO-2), physiologically inhibits carotid body activity. Because HO-2 requires molecular $O_2$ for activity, stimulation of carotid body activity by hypoxia reflects, in part, reduced formation of CO.

Like CO, hydrogen sulfide ($H_2S$) is a gasotransmitter physiologically regulating neuronal transmission and vascular tone. Cystathionine γ-lyase (CSE; EC 4.4.1.1) and cystathionine β-synthase (CBS; 4.2.1.22) are enzymes associated with generation of endogenous $H_2S$. CBS is the predominant $H_2S$ synthesizing enzyme in the brain, while CSE preponderates in the peripheral tissues. Heme-oxygenases are enzymes associated with generation of endogenous CO.

Cystathionine γ-Lyase Enzyme (CSE)

CSE catalyzes the formation of cysteine from cystathionine, and also generates $H_2S$ from cyst(e)ine. In some embodiments, CSE-derived-$H_2S$, a redox active gasotransmitter, plays a role in hypoxic sensing by the carotid body. Genetic or pharmacologic deletion of CSE impairs hypoxic sensing by the carotid body as well as in neonatal adrenal medullary chromaffin cells (AMC).

CSE is expressed in rat and mouse glomus cells, the main site of $O_2$ sensing in the carotid body. Described herein is a physiological role for $H_2S$ generated by CSE in mediating hypoxic sensing by the carotid body. Chemoreceptor responses to acute hypoxia were markedly impaired in CSE knockout mice and following pharmacologic inhibition of CSE. Although hypoxic sensitivity was lost, sensory response to $CO_2$ was intact in mutant mice and CSE inhibitor treated rats. Carotid bodies are the primary mediators of ventilatory stimulation by acute hypoxia. $CSE^{-/-}$ mice exhibited selective loss of ventilatory response to hypoxia but not to $CO_2$, suggesting that CSE disruption impacts systemic responses to acute hypoxia by affecting the carotid body. CSE is also expressed in neonatal adrenal medullary chromaffin cells (AMC) of rats and mice whose hypoxia-evoked catecholamine secretion is greatly attenuated by CSE inhibitors and in $CSE^{-/-}$ mice.

Described herein is the carotid body response to hypoxia in wild type ($CSE^{+/+}$) and $CSE^{-/-}$ mice as well as in rats treated with a CSE inhibitor. The following observations indicate that $H_2S$ generated by CSE mediates carotid body hypoxic sensing. First, hypoxia increased $H_2S$ generation in the carotid body in a stimulus-dependent manner, an effect that was lost in $CSE^{-/-}$ mice as well as in rats treated with a CSE inhibitor. Second, loss of hypoxia-evoked $H_2S$ generation paralleled impaired hypoxic sensing by the carotid body. Third, an $H_2S$ donor, but not L-cysteine, stimulated the carotid body with a time-course and magnitude comparable to that evoked by low $O_2$. An $H_2S$ donor stimulated carotid body activity in CSE knockout mice, indicating that the loss of hypoxic sensitivity is due to absence of $H_2S$ generation rather than impaired $H_2S$ signaling. These findings demonstrate that during hypoxia, CSE is a source of $H_2S$ generation in the carotid body, and suggest that CSE contributes to hypoxic sensing by catalyzing $H_2S$ generation.

Heme Oxygenase—2 (HO2)

Under normoxia, sensory activity and basal $H_2S$ generation in the carotid bodies is low. As HO-2 is an $O_2$ requiring enzyme, low normoxemic sensory activity reflects tonic inhibition by CO generated by HO-2 in the carotid body. Described herein are studies that show that inhibitory influence by the HO-2-CO system plays a role in low normoxic levels of $H_2S$. An HO-2 inhibitor not only markedly elevated basal $H_2S$ levels but also augmented baseline sensory activity and potentiated hypoxic response in $CSE^{+/+}$ mice. These effects were absent in $CSE^{-/-}$ mice, implying that HO-2 tonically inhibits CSE. CO generated by HO-2 mediates the inhibition of $H_2S$ generation from CSE. A CO donor inhibited $H_2S$ generation during hypoxia. CO interacts with CBS, another enzyme that generates $H_2S$, by binding to its heme moiety. Given that CSE is not a heme containing enzyme; it is likely that CO inhibits CSE activity by interacting with histidine residues, as it does with other proteins. Thus, CO physiologically inhibits the $CSE-H_2S$ system with hypoxia reducing HO-2 activity to reverse the inhibition and augment $H_2S$ formation.

Ion Channels Associated with Carotid Body Activity

Although KATP channels are targets of $H_2S$, glibenclamide, a potent inhibitor of KATP channels, was ineffective in preventing carotid body stimulation by NaHS or hypoxia. On the other hand, $Ca^{2+}$ influx plays a role in carotid body stimulation by $H_2S$ as well as hypoxia. In some instances, $Ca^{2+}$ influx via high voltage-gated $Ca^{2+}$ channels, especially the L-type, plays a role in carotid body stimulation by hypoxia. L-type $Ca^{2+}$ channels in glomus cells are redox sensitive, activated by hypoxia, and inhibited under normoxia. A recent study demonstrated that $H_2S$ signaling involves covalent modification of redox sensitive cysteine residues in proteins through S-sulfhydration. In some instances, $H_2S$ generated by hypoxia activates L-type $Ca^{2+}$ channels in glomus cells via S-sulfhydration. In addition, $H_2S$ affects $Ca^{2+}$-activated $K^+$ currents in glomus cells.

Carotid Body Activity in Neonates

Carotid bodies are the main organs for sensing acute hypoxia in adults but in neonates they are relatively insensitive to low $O_2$. On the other hand, adrenal medullary chromaffin cells (AMC) are extremely sensitive to hypoxia in neonates, and low $O_2$ stimulates catecholamine secretion, which plays a role in maintaining homeostasis in neonates under hypoxic stress. Like glomus cells, neonatal AMC expressed CSE, and hypoxia-evoked catecholamine secretion was severely impaired in $CSE^{-/-}$ mice and in rats treated with a CSE inhibitor. Since hypoxia also increased $H_2S$ generation in adrenal glands, $CSE-H_2S$ system mediates acute hypoxic sensing by neonatal AMC. Hypoxic sensitivity of AMC, however, declines with age. In some instances, AMC is associated with developmental decline in CSE expression.

Gasotransmitters

Physiologically, the carotid body is sensitive to changes in arterial blood flowing through it including changes in partial pressure of oxygen in arterial blood ($PaO_2$) (e.g., hypoxia), and/or changes in partial pressure of carbon dioxide in arterial blood ($PaCO_2$) (e.g., hypocapnia, hypercapnia). Certain gasotransmitters are involved in hypoxic sensing by the carotid body including, and not limited to carbon monoxide, and hydrogen sulfide ($H_2S$).

Described herein are studies that show that hydrogen sulfide ($H_2S$) is a physiologic gasotransmitter of the carotid body, enhancing its sensory response to hypoxia. Glomus cells, the site of $O_2$ sensing in the carotid body, express cystathionine gamma lyase (CSE), an $H_2S$ generating enzyme, with hypoxia increasing $H_2S$ generation in a stimulus-dependent manner. Mice with genetic deletion of CSE display severely impaired carotid body response and ventilatory stimulation to hypoxia as well as a loss of hypoxia-evoked $H_2S$ generation. Pharmacologic inhibition of CSE elicits a similar phenotype in mice and rats. Hypoxia-evoked $H_2S$ generation in the carotid body is regulated by interaction of CSE with hemeoxygenase-2, which generates carbon monoxide.

In some instances, inhibition of HO-2 reduces production of CO, thereby increasing the production of $H_2S$ with subsequent augmentation of carotid body activity. In other embodiments, inhibition of CSE reduces production of $H_2S$ thereby blunting the activity of the carotid body.

Chemical Control of Ventilation

In normal individuals, balanced activity of two enzymes, cystathionine γ-lyase enzyme (CSE) and heme oxygenase-2 (HO-2), maintains adequate oxygenation during both waking and sleeping states. The enzyme CSE generates $H_2S$ which in turn stimulates the activity of the carotid body. The enzyme HO-2 generates CO which serves as a gasotransmitter signal that suppresses $H_2S$ generation by CSE, thereby reducing the activity of the carotid body.

Thus, where an individual suffers from a sleep-related breathing disorder that involves hyperventilation, inhibition of CSE in glomus cells reduces activity of the carotid body, with concomitant dampening of carotid sinus nerve activity. Where an individual suffers from a sleep-related breathing disorder that involves hypoventilation, inhibition of HO-2 reduces CO generation. Lower levels of CO result in increased generation of $H_2S$ by the CSE, thereby up-regulating the activity of the carotid body. Accordingly, provided herein are methods of treatment of disordered breathing comprising modulation (e.g., down-regulation, up-regulation) of gasotransmitter pathways implicated in the chemical control of breathing. In some embodiments, provided herein are methods of treatment of sleep disordered breathing comprising down-regulation of gasotransmitter pathways implicated in the chemical control of breathing (e.g., by reducing the production of $H_2S$ and/or CO in the carotid body). In some embodiments, provided herein are methods of treatment of sleep disordered breathing comprising up-regulation of gasotransmitter pathways implicated in the chemical control of breathing (e.g., by increasing the production of $H_2S$ and/or CO in the carotid body).

Definitions

As used herein, the term "treatment", "treat", or "treating" in some embodiments includes achieving a therapeutic benefit. Therapeutic benefit is meant to include eradication or amelioration of the underlying disorder or condition being treated. For example, therapeutic benefit includes alleviation or partial and/or complete halting of the sleep-related breathing disorder. Also, a therapeutic benefit is achieved with the eradication or amelioration of one or more of the physiological or psychological symptoms associated with the underlying condition such that an improvement is observed in the patient, notwithstanding the fact that the patient is still affected by the condition. For example, in an individual suffering from sleep apnea, therapeutic benefit includes alleviation or partial and/or complete halting of sleep fragmentation, or reduction in frequency of arousals or awakenings or reduction in incidence of awakenings. In some embodiments, "treatment" provides prophylactic benefit including prevention of a condition, retarding the progress of a condition, or decreasing the likelihood of occurrence of a condition (e.g., prevention of sleep apnea in an individual who has been prescribed opioids for a chronic condition, reducing the incidence of sleep apnea in said individual or the like). As used herein, "treat", "treating" or "treatment" includes prophylaxis.

"Activity of the carotid body" refers to the response of the carotid body to various signals. In some embodiments, such signals include $pCO_2$ or $pO_2$ in arterial blood. In some embodiments, such signals include presence or absence of certain gasotransmitters such as CO or $H_2S$ in the carotid body or in the vicinity of the carotid body. In some embodiments, such signals include presence or absence of certain ions such as $Ca^{2+}$ or $K^+$ ions in the carotid body or in the vicinity of the carotid body. In some embodiments, such signals include action potentials of the nerves that innervate the carotid body.

"Chemosensitivity" of the carotid body refers to the magnitude of the response of the carotid body to a known level of stimulation by chemical messengers including and not limited to $O_2$, $CO_2$, CO, and $H_2S$. Increased chemosensitivity is defined as an increased and disproportionate response to one that is observed under normal physiologic conditions to a similar stimulus.

Sleep-related breathing disorder (SRBD) refers to an abnormal respiratory pattern (e.g., apneas, hypopneas, or respiratory effort related arousals) or an abnormal reduction in gas exchange (e.g., hypoventilation, hyperventilation, intermittent ventilation) during sleep. SRBD alters sleep duration and architecture, and if repetitive, results in daytime symptoms, signs, or organ system dysfunction. SRBD includes obstructive sleep apnea (OSA), central sleep apnea (CSA), mixed apnea, hypopnea, hypercapnia, hypocapnia, central sleep apnea syndrome (CSAS), idiopathic central sleep apnea (ICSA), Cheyne-Stokes breathing-central sleep apnea (CSB-CSA), obesity hypoventilation syndrome (OHS), alveolar hypoventilation syndromes, congenital central hypoventilation syndrome (CCHS), high altitude periodic breathing, CSA due to a medical condition, CSA due to a drug or substance (e.g., narcotic-induced CSA, opioid-induced CSA), obstructive sleep apnea syndrome (OSAS), chronic mountain sickness, and/or sleep-related breathing disorders associated with neurologic conditions or neuromuscular conditions as described herein.

As used herein, the term "inhibitor" refers to a molecule which is capable of inhibiting (including partially inhibiting or allosteric inhibition) one or more of the biological activities of a target molecule, e.g., CSE, HO-2 or the like. Inhibitors act, for example, by reducing or suppressing the activity of a target molecule and/or reducing or suppressing signal transduction. In some embodiments, an inhibitor described herein causes substantially complete inhibition of the target molecule (e.g., CSE, HO-2 or the like). In some embodiments, an inhibitor is a partial inhibitor. The phrase "partial inhibitor" refers to a molecule which can induce a partial response for example, by partially reducing or suppressing the activity of a target molecule and/or partially reducing or suppressing signal transduction. In some instances, a partial inhibitor mimics the spatial arrangement, electronic properties, or some other physicochemical and/or biological property of the inhibitor. In some instances, in the presence of elevated levels of an inhibitor, a partial inhibitor competes with the inhibitor for occupancy of the target molecule and provides a reduction in efficacy, relative to the inhibitor alone. In some embodiments, an inhibitor described herein is an allosteric modulator of a target molecule (e.g., CSE, HO-2 or the like). As used herein, "substantially complete inhibition" means, for example, >95% inhibition of one or more targeted molecules (e.g., CSE, HO-2 or the like). In other embodiments, "substantially complete inhibition" means, for example, >90% inhibition of one or more targeted molecules (e.g., CSE, HO-2 or the like). In some other embodiments, "substantially complete inhibition" means, for example, >80% inhibition of one or more targeted molecules (e.g., CSE, HO-2 or the like). As used herein, "partial inhibition" means, for example, between about 40% to about 60% inhibition of one or more targeted molecules (e.g., CSE, HO-2 or the like). In other embodiments, "partial inhibition" means, for example, between about 50% to about 70% inhibition of one or more targeted molecules (e.g., CSE, HO-2 or the like).

"Apnea" is the cessation, or near cessation, of airflow. It exists when airflow is less than 20 percent of baseline for at least 10 seconds in adults. These criteria may vary among sleep laboratories and in children. Apnea is most commonly detected using sensors placed at the nose and mouth of the sleeping patient. Inspiratory airflow is typically used to identify an apnea, although both inspiratory and expiratory airflow are usually abnormal. Some laboratories use surrogate measures instead, such as inspiratory chest wall expansion. Three types of apnea are observed during sleep:

An "obstructive apnea" occurs when airflow is absent or nearly absent, but ventilatory effort persists. It is caused by complete, or near complete, upper airway obstruction. Obstructive apnea includes upper airway apnea and peripheral apnea. Obstructive hypopneas are due to partial upper airway obstruction, which is often accompanied by snoring and inspiratory flow limitation.

A "central apnea" occurs when both airflow and ventilatory effort are absent. Breathing cessation is proven by an absence of diaphragmatic activation, measured by electromyography (EMG). Central hypopneas are due to reduced inspiratory effort.

During a "mixed apnea," there is an interval during which there is no respiratory effort (i.e., central apnea pattern) and an interval during which there are obstructed respiratory efforts. The central apnea pattern usually precedes the obstructive apnea pattern during mixed apnea.

"Hypopnea" is a reduction of airflow insufficient to meet the criteria for an apnea. It exists when all of the following four criteria are met, according to the current definition: airflow decreases at least 30 percent from baseline, there is diminished airflow lasting at least 10 seconds, at least 90 percent of the duration of diminished airflow is spent with airflow that is at least 30 percent less than baseline, and decreased airflow is accompanied by at least 4 percent oxyhemoglobin desaturation. Alternative scoring criteria exist. The most recent definition, endorsed by the American Academy of Sleep Medicine, recommends that hypopnea be scored when all of the following four criteria are met: airflow decreases at least 30 percent from baseline; there is diminished airflow lasting at least 10 seconds; at least 90 percent of the duration of diminished airflow is spent with airflow that is at least 30 percent less than baseline; decreased airflow is accompanied by at least 4 percent oxyhemoglobin desaturation. Alternative scoring criteria are also endorsed: airflow decreases at least 50 percent from baseline; there is diminished airflow lasting at least 10 seconds; at least 90 percent of the duration of diminished airflow is spent with airflow that is at least 30 percent less than baseline; decreased airflow is accompanied by at least 3 percent oxyhemoglobin desaturation or an arousal. Like apnea, hypopnea is detected using sensors or surrogate measures, such as chest wall expansion. Inspiratory airflow is typically used to identify a hypopnea, although both inspiratory and expiratory airflow are usually abnormal.

"Eupnea" is normal, unlabored ventilation, i.e., resting respiration

"Hypercapnia" or "hypercarbia" is the presence of excess $CO_2$ in the blood.

"Hypocapnia" is a state of reduced $CO_2$ in the blood.

Respiratory effort related arousals (RERAs) exist when there is a sequence of breaths that lasts at least 10 seconds, is characterized by increasing respiratory effort or flattening of the nasal pressure waveform, and leads to an arousal from sleep, but does not meet criteria of an apnea or hypopnea. The inspiratory airflow or tidal volume is maintained during these episodes, but requires increased respiratory effort. RERAs are often accompanied by a terminal snort or an abrupt change in respiratory measures. Daytime sleepiness, fatigue, or inattention can result from microarousals (i.e., electroencephalographic activation lasting three seconds or less), despite the absence of apneas or hypopneas. Snoring may or may not be a prominent complaint. These symptoms are reduced by treatment that alleviates RERAs. RERAs (>5 events per hour) that are associated with daytime sleepiness are a subtype of obstructive sleep apnea (OSA), also called Upper Airway Resistance Syndrome (UARS).

The Apnea-hypopnea index (AHI) is the average total number of apneas and hypopneas per hour of sleep.

The respiratory disturbance index (RDI) is the average total number of events (e.g., apneas, hypopneas, and RERAs) per hour of sleep.

The oxygen desaturation index (ODI) is the average number of times that the oxygen saturation falls by more than 3 or 4 percent per hour of sleep.

The arousal index (ArI) is the average total number of arousals or awakenings per hour of sleep. It is generally lower than the AHI or RDI because approximately 20 percent of apneas or hypopneas are not accompanied by arousals that are evident on polysomnography. However, the ArI can be greater than the AHI or RDI if arousals occur due to causes other than apneas or hypopneas. As examples, arousals can be caused by periodic limb movements, noise, and sleep state transitions.

Central sleep apnea syndrome (CSAS) includes idiopathic primary central sleep apnea (ICSA), primary central sleep apnea (CSA), Cheyne-Stokes breathing, high altitude periodic breathing, CSA due to a medical condition, and CSA due to a drug or substance.

"Obstructive sleep apnea syndrome" encompasses obstructive sleep apnea (OSA) in adults and OSA in children. OSA in adults is defined as either more than 15 apneas, hypopneas, or RERAs per hour of sleep (i.e., an AHI or RDI>15 events/hr) in an asymptomatic patient, or more than 5 apneas, hypopneas, or RERAs per hour of sleep (i.e., an AHI or RDI>5 events per hour) in a patient with symptoms (e.g., sleepiness, fatigue and inattention) or signs of disturbed sleep (e.g., snoring, restless sleep, and respiratory pauses).

Primary CSA exists when symptoms or signs of disturbed sleep are accompanied by more than five central apneas plus hypopneas per hour of sleep, and normocarbia during wakefulness. The threshold frequency of events that warrants treatment beyond that required for the underlying disease is unknown.

Cheyne-Stokes breathing refers to a cyclic pattern of crescendo-decrescendo tidal volumes and central apneas, hypopneas, or both. It is commonly associated with heart failure or stroke.

Patients with a "hypoventilation syndromes" generally have mild hypercarbia or elevated serum bicarbonate levels when awake, which worsen during sleep. Hypoventilation syndromes include, and are not limited to, congenital central hypoventilation syndrome (CCHS) and obesity hypoventilation syndrome (OHS).

"Hypoventilation" during sleep is defined as an increase in the arterial carbon dioxide ($PaCO_2$) of 10 mm Hg during sleep (compared with an awake supine value) that lasts at least 25 percent of the sleep time. Directly measuring the $pCO_2$ in an arterial blood gas during a sleep study is optimal, but impractical. Transcutaneous $CO_2$ measurements and expired end-tidal $CO_2$ are alternatives, but are not sufficiently accurate for routine studies. Sleep hypoventilation is usually presumed when persistent oxyhemoglobin desaturation is detected without an alternative explanation, such as apnea or hypopnea.

Diseases and Conditions

Provided herein are methods for treatment of diseases and conditions that are associated with hypoxic sensing by the carotid body comprising administration of agents that modulate carotid body activity (e.g., CSE inhibitors, HO-2 inhibitors, $H_2S$ donors, CO donors) to individuals in need thereof. Hypoxic sensing by the carotid body plays a role in regulation of breathing. In mammals, the carotid body comprises peripheral chemoreceptors that are associated with control of ventilation in response to oxygen and/or carbon dioxide levels in blood. The carotid body is also linked to the central chemoreceptors found in the brainstem; interaction of the peripheral and central chemoreceptors controls ventilation in mammals. Accordingly, further provided herein are methods of treatment of diseases or conditions that are associated with carotid body activity and/or control of ventilation and/or breathing in individuals in need thereof. In some embodiments, diseases or conditions that are associated with carotid body activity and/or control of ventilation and/or breathing in individuals are sleep-related breathing disorders. In some embodiments, provided herein are methods for treatment of sleep-related breathing disorders comprising administration of agents that modulate carotid body activity (e.g., CSE inhibitors, HO-2 inhibitors, $H_2S$ donors, CO donors) to individuals in need thereof. In some embodiments, provided herein are methods for treatment of sleep-related breathing disorders comprising administration of CSE inhibitors to individuals in need thereof. In some embodiments, provided herein are methods for treatment of sleep-related breathing disorders comprising administration of HO-2 inhibitors to individuals in need thereof. In some embodiments, provided herein are methods for treatment of sleep-related breathing disorders comprising administration of $H_2S$ donors to individuals in need thereof. In some embodiments, provided herein are methods for treatment of sleep-related breathing disorders comprising administration of CO donors to individuals in need thereof.

Sleep-Related Breathing Disorders

Sleep-related breathing disorders, or sleep-disordered breathing, refer to an abnormal respiratory pattern (e.g., apneas, hypopneas, or respiratory effort related arousals) or an abnormal reduction in gas exchange (e.g., hypoventilation) during sleep. Sleep-related breathing disorders are identified using polysomnography (PSG) that has captured one or more periods of rapid eye movement (REM) sleep; severe perturbations occur during REM sleep.

In healthy humans, sleep induces loss of upper airway muscle tone (patency), increase in upper airway resistance and/or intrathoracic pressure swings. Mild $CO_2$ retention (hypercapnia) and/or respiratory acidosis during sleep do not cause significant arterial $O_2$ desaturation or compromised systemic $O_2$ transport in healthy individuals. However, in individuals suffering from anatomically compromised airway patency (e.g., obese individuals) or individuals whose ventilatory control systems are aberrantly driven by chemical stimuli. Loss of wakefulness produces instability of central respiratory motor output and breathing pattern in sleep. Sleep-disordered breathing contributes to short and long-term consequences to health.

The sensory response of the carotid body and regulation of breathing is dependent on changes in arterial oxygenation. Accordingly, in some embodiments, provided herein are methods for treatment of sleep-disordered breathing comprising administration of agents that modulate the activity of the carotid body (e.g., CSE inhibitors or partial inhibitors, HO-2 inhibitors or partial inhibitors, $H_2S$ donors or any other agents described herein) to individuals in need thereof. Sleep-related breathing disorders are conditions that manifest as (a) momentary, often cyclical cessations of breathing rhythms (apneas); or (b) momentary or sustained reduction in breath amplitude (hypopneas) that are sufficient to cause arterial hypoxemia and hypercapnia or (c) a combination thereof. The ventilatory deficiencies are often manifested during sleep (sleep apnea) and lead to intermittent awakening from the sleep state. In some instances, such intermittent arousal from the sleep state (sleep fragmentation) also leads to increased compensatory responses of the autonomic nervous system.

Sleep disordered breathing causes repeated episodes of ventilatory overshoots and undershoots and swings in arterial blood gases and/or intrathoracic pressure. Anomalies in both anatomical and neurochemical control of upper airway and/or other respiratory musculature can trigger cyclical apnea. Patients with recurrent apnea experience periodic hypoxemia or intermittent hypoxia and are prone to autonomic morbidities including hypertension. In rodent models chronic intermittent hypoxia enhances carotid body responses to hypoxia, and the ensuing chemo-reflex mediates increases in sympathetic nerve activity resulting in elevated blood pressure.

Central Sleep Apnea Syndrome

Apnea is associated with a reduction or cessation of brain stem respiratory output. Central sleep apnea syndrome (CSAS) can be idiopathic (primary central sleep apnea (CSA)) or secondary. Examples of secondary CSAS include Cheyne-Stokes breathing (CSB), CSA due to high altitude periodic breathing, CSA due to a medical condition, and/or CSA due to a drug or substance.

The carotid body comprises peripheral chemoreceptors that are linked to the chemoreceptors found in the brainstem. The carotid body controls ventilation by monitoring oxygen and/or carbon dioxide levels in arterial blood. Accordingly, in some embodiments, provided herein are methods for treatment of Central Sleep Apnea comprising administration of agents that modulate the activity of the carotid body (e.g., CSE inhibitors or partial inhibitors, HO-2 inhibitors or partial inhibitors, $H_2S$ donors, CO donors or any other agents described herein) to individuals in need thereof.

Cheyne-Stokes Breathing—Central Sleep Apnea (CSB-CSA)

Congestive heart failure patients suffer from a form of non-hypercapnic central sleep apnea characterized by a waxing (crescendo) and waning (decrescendo) pattern of ventilation in which breathing is rapid for a period and then absent for a period (Cheyne-Stokes breathing). Arterial $pCO_2$ is in a low to normal range. Hyperventilation is triggered during sleep which causes a ventilatory overshoot and hypocapnia. Ventilatory drive decreases subsequent to hypocapnia resulting in a cessation of breathing (apnea). Apnea is then followed by hypercapnia and hypoxia. The carotid body then responds to changes in arterial oxygenation (hypoxia) resulting in increased activity of the carotid body which then triggers hyperventilation. The result is a Cheyne-Stokes breathing pattern associated with central sleep apnea (CSB-CSA). In some embodiments, increased activity of the carotid body in individuals suffering from or suspected to be suffering from CSB-CSA causes an increase of the loop gain in the ventilatory drive control system.

In some embodiments, inhibition of CSE reduces $H_2S$ generation, thereby reducing the chemosensitivity of the carotid body. A reduction in carotid body sensitivity reduces loop gain of the ventilatory drive control system and blunts hyperventilation. Hypocapnia is reduced which prevents overshoot of $pCO_2$ below the threshold and prevents apnea.

Accordingly, described herein are methods for treatment of CSB-CSA comprising administration of CSE inhibitors to individuals in need thereof (e.g., individuals suffering from or suspected to be suffering from CSB-CSA). Also described herein are methods for decreasing the activity (e.g., chemosensitivity) of the carotid body comprising administration of CSE inhibitors to individuals in need thereof (e.g., individuals suffering from or suspected to be suffering from CSB-CSA). In some embodiments, administration of a CSE inhibitor to an individual suffering from or suspected to be suffering from CSB-CSA reduces loop gain of the ventilatory drive control system in the individual. In some of the aforementioned embodiments, administration of a CSE inhibitor to an individual in need thereof lowers blood pressure in the individual. In some of the aforementioned embodiments, administration of a CSE inhibitor to an individual in need thereof dampens carotid sinus nerve activity thereby reducing or preventing the occurrence of CSB-CSA.

Obesity Hypoventilation Syndrome

Obese individuals suffer from loss of patency of airway muscles and a form of hypercapnic central sleep apnea characterized by hypoventilation during sleep. Arterial $pCO_2$ is above normal range (>45 mm Hg). Hypoventilation worsens during sleep. Hypoventilation reduces ventilatory drive.

In some embodiments, inhibition of HO-2 reduces CO generation thereby increasing CSE-mediated $H_2S$ generation. An increase in $H_2S$ generation increases carotid body activity, thereby increasing respiratory drive.

Accordingly, described herein are methods for treatment of OHS comprising administration of HO-2 inhibitors or $H_2S$ donors to individuals in need thereof (e.g., individuals suffering from or suspected to be suffering from OHS). Also described herein are methods for increasing the activity (e.g., chemosensitivity) of the carotid body comprising administration of HO-2 inhibitors or $H_2S$ donors to individuals in need thereof (e.g., individuals suffering from or suspected to be suffering from obesity hypoventilation syndrome and/or other alveolar hypoventilation syndromes). In some of the aforementioned embodiments, administration of a HO-2 inhibitor or a $H_2S$ donor to an individual suffering from or suspected to be suffering from obesity hypoventilation syndrome and/or other alveolar hypoventilation syndromes increases carotid sinus nerve activity thereby reducing or preventing the occurrence of OHS. In some of the aforementioned embodiments, a HO-2 inhibitor or a $H_2S$ donor is a respiratory stimulant.

Idiopathic CSA

In some embodiments, provided herein are methods for treatment of idiopathic CSA comprising administration of agents that modulate carotid body activity (e.g., CSE inhibitors, HO-2 inhibitors, $H_2S$ donors, CO donors) to individuals in need thereof. In certain individuals, CSA is of unknown origin and results in repeated pauses in breathing effort and airflow.

Congenital Central Hypoventilation Syndrome (CCHS)

In some embodiments, provided herein are methods for treatment of congenital central hypoventilation syndrome comprising administration of agents that modulate carotid body activity (e.g., CSE inhibitors, HO-2 inhibitors, $H_2S$ donors, CO donors) to individuals in need thereof.

CCHS, or Congenital Central Hypoventilation Syndrome, is a disorder wherein control of breathing is absent or impaired. A CCHS child's respiratory response to low blood oxygen saturation (hypoxia) or to $CO_2$ retention (hypercapnia) is typically sluggish during awake hours and absent, or reduced during sleep, serious illness, and/or stress.

Narcotic-Induced Sleep Apnea

In some embodiments, provided herein are methods for treatment of narcotic-induced sleep apnea (e.g., opioid induced sleep apnea) comprising administration of agents that modulate carotid body activity (e.g., CSE inhibitors, HO-2 inhibitors, $H_2S$ donors, CO donors) to individuals in need thereof. Further provided herein are methods for treatment of opioid-induced sleep apnea comprising administration of agents that modulate carotid body activity (e.g., CSE inhibitors, HO-2 inhibitors, $H_2S$ donors, CO donors) to individuals in need thereof. As used herein the term "narcotics" includes opium, opiates, derivatives of opium and opiates, including their isomers, esters, ethers, and salts; poppy straw and/or concentrate of poppy straw; coca leaves and extracts of coca leaves; cocaine, its salts, optical and geometric isomers, and salts of isomers; ecgonine and salts thereof; and the like. By way of example, opioids are used for chronic pain treatment for cancer patients, and as long-term therapy for chronic pain unrelated to cancer. Studies (Webster L. R., et al., *Pain Med.* 2008: 9(4):425-432) show a higher incidence of sleep disordered breathing in opioid treated chronic pain patients compared to the general population. Accordingly, in some embodiments, carotid body modulators (e.g., CSE inhibitors or partial inhibitors, HO-2 inhibitors or partial inhibitors, $H_2S$ donors, CO donors described herein) alleviate or reduce the incidence of sleep apnea in individuals undergoing treatment with narcotics (e.g., opioids). Examples of opiods that induce sleep apnea include and are not limited to morphine, codeine, oxycodone, hydrocodone, dihydromorphine, pethidine, methadone and the like. Other agents that exert a similar influence on the cerebral opioid receptor system are also contemplated within the scope of embodiments presented herein, such as, for example, buprenorphine, tramadol, and the like.

Neurologic Conditions

In some embodiments, provided herein are methods for treatment of sleep-related disorders associated with neurologic and/or neuromuscular conditions comprising administration of agents that modulate carotid body activity (e.g., CSE inhibitors, HO-2 inhibitors, $H_2S$ donors, CO donors) to individuals in need thereof.

In some instances, neurological conditions that are associated with impaired tone of the upper airway muscles cause sleep-related breathing disorders. Obstructive sleep apnea occurs in individuals suffering from impaired airway patency especially when the individual has additional risk factors, such as obesity or hypothyroidism. Obstruction occurs at the pharyngeal level because of weakness in the diaphragm and/or intercostal muscles with subsequent inability to overcome changes in airway resistance. Apnea is magnified during rapid eye movement (REM) sleep due to the natural loss of intercostal muscle tone during that period.

Neurologic disorders associated with incidence of sleep-related breathing disorder include and are not limited to myasthenia gravis (neuromuscular junction), amyotrophic lateral sclerosis (motor neuron disease), post-polio syndrome, myopathies (e.g., acid maltase deficiency), congenital myopathies, neuropathies, myotonic dystrophy, Duchenne's dystrophy, mitochondrial encephalomyopathy, stroke, epilepsy, Parkinsonism, Alzheimer's disease, and Huntington's disease. Neuromuscular disorders associated with sleep-related breathing disorders in children include, but are not limited to Duchenne's dystrophy, myotonic dystrophy, nemaline myopathy congenital muscular dystrophy, cerebral palsy, spinal muscular atrophy, transverse myelitis, and poliomyelitis.

Chronic Intermittent Hypoxia

In some embodiments, provided herein are methods for treatment of chronic intermittent hypoxia comprising administration of agents that modulate carotid body activity (e.g., CSE inhibitors, HO-2 inhibitors, $H_2S$ donors, CO donors) to individuals in need thereof.

Chronic intermittent hypoxia occurs in certain physiological and/or pathophysiological conditions and causes increased blood pressure, elevated circulating catecholamines, enhanced long term facilitation of the respiratory motor activity and/or augmented sympathetic nerve activity. In some embodiments, modulation of carotid body activity reduces or prevents occurrence of CIH. In some instances, chronic intermittent hypoxia (CIH) is associated with increased chemosensitivity of the carotid body. In some instances increased chemosensitivity of the carotid body results in increased loop gain of the ventilatory drive system. Accordingly, in some embodiments, inhibiting CSE reduces carotid body activity, thereby attenuating the loop gain.

CSE Inhibitors

In some embodiments, methods of treating sleep-related breathing disorders comprise administration of a therapeutically effective amount of a CSE inhibitor to an individual in need thereof. In some of such embodiments, CSE inhibitors blunt the activity of the carotid body. Compounds that inhibit cystathionine γ-lyase enzyme (CSE) include, for example DL-propargylglycine (PAG), beta cyano L-alanine (BCA). CSE inhibitors include analogs of PAG and/or BCA that retain inhibitory activity towards the enzyme. Also contemplated as CSE inhibitors are compounds that inhibit pyridoxal 5' phosphate. Some examples of inhibitors of pyridoxal 5' phosphate include e.g., aminooxyacetate, hydroxylamine and the like.

HO-2 Inhibitors

In some embodiments, methods of treating sleep-related breathing disorders comprise administration of a therapeutically effective amount of a HO-2 inhibitor to an individual in need thereof. In some of such embodiments, HO-2 inhibitors are respiratory stimulants and augment the activity of the carotid body. Compounds that inhibit hemeoxygenase-2 (HO-2) include, for example, Cr(III) Mesoporphyrin IX chloride, or other tin or zinc porphyrins. In some embodiments, HO-2 inhibitors include compounds described by Kinobe et al. in *Can. J. Physiol. Pharmacol.*, 2008, 86, 577-599; and in *J. Pharmacol. Expt. Ther.* 2007, 323, 763-770; hemeoxygenase inhibitors described therein are incorporated herein by reference. In some embodiments, HO-2 inhibitors suitable for methods described herein include:

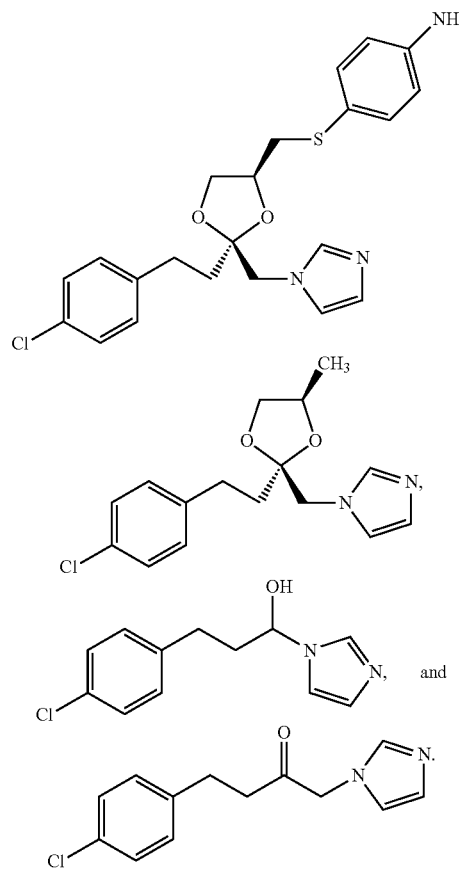

$H_2S$ Donors

In some embodiments, methods of treating sleep-related breathing disorders comprise administration of a therapeutically effective amount of an $H_2S$ donor compound to an individual in need thereof. In some of such embodiments, $H_2S$ donors are respiratory stimulants and augment the activity of the carotid body. Compounds that are $H_2S$ donors include compounds described by Caliendo et al. *J. Med. Chem.*, May 2010 [Epub ahead of print], $H_2S$ donors described therein are incorporated herein by reference. In some embodiments, $H_2S$ donors suitable for methods described herein include:

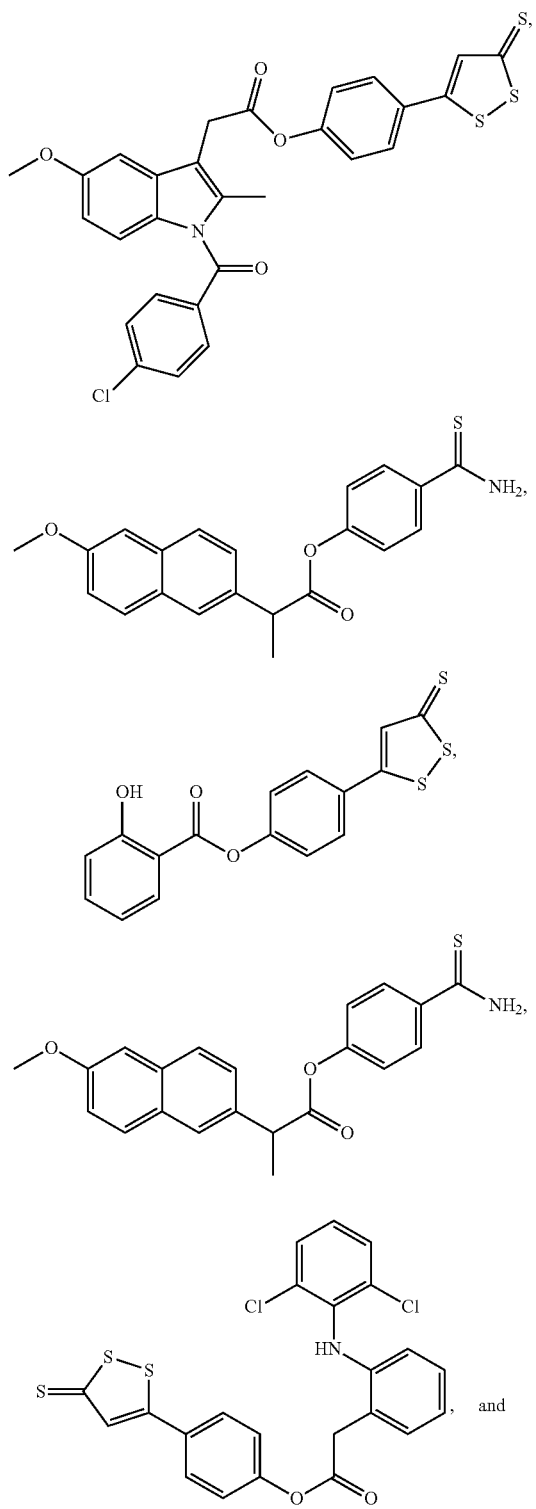

-continued

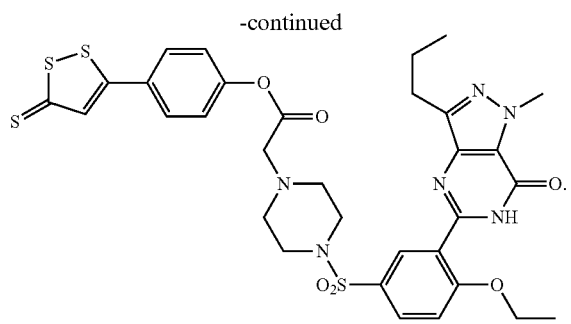

In some embodiments, a suitable $H_2S$ donor comprises a known respiratory stimulant (e.g., acetazolamide) attached to a $H_2S$ donor group. By way of example, a suitable $H_2S$ donor agent is synthesized using known synthetic procedures as described in, Caliendo et al. *J. Med. Chem.*, May 2010 [Epub ahead of print].

CO Donors

In some embodiments, methods of treating sleep-related breathing disorders comprise administration of a therapeutically effective amount of a CO donor compound to an individual in need thereof. In some of such embodiments, CO-donors are respiratory stimulants and blunt the activity of the carotid body. Compounds that are CO donors include tricarbonyldichlororuthenium(II) dimer $[Ru(CO)_3Cl_2]_2$, tricarbonylchloro(glycinato)ruthenium(II) $[Ru(CO)_3Cl(glycinate)]$, and the like. In some embodiments, administration of a CO donor compound decreases production of $H_2S$, thereby reducing the activity of the carotid body.

Combination Therapy

In some embodiments, an agent that modulates the activity of the carotid body (e.g., CSE inhibitors, HO-2 inhibitors, $H_2S$ donors, CO donors) is administered in combination with a second therapeutic agent. In some embodiments, a second therapeutic agent is an agent that stimulates respiratory drive. In some embodiments, a second therapeutic agent induces metabolic acidosis, thereby increasing respiratory drive. In some embodiments, a second therapeutic agent treats symptoms such as hypertension that are associated with sleep apneas. In some embodiments, a second therapeutic agent is a sleep inducing agent.

Examples of agents suitable for combination therapy with an agent that modulates the activity of the carotid body include carbonic anhydrase inhibitors (e.g., acetazolamide), cholinesterase inhibitors (e.g., donepezil), adenosine inhibitors (e.g., theophylline), progestational agents (e.g., progestone), opiod antagonists (e.g., naloxone), central nervous system stimulants (e.g., nicotine), serotonergic agents (e.g., paroxetine) including selective serotonin reuptake inhibitors (SSRIs), antidepressants (e.g., protriptyline) including conventional and/or tricyclic antidepressants, antihypertensives (e.g., metoprolol, cilazapril, propranolol, atenolol, hydrochlorothiazide), calcium channel antagonists (e.g., isradipine), ACE inhibitors (e.g., spirapril), respiratory stimulants (e.g., doxapram), alpha-2 adrenergic agonists (e.g., clonidine), gama aminobutyric acid agonists (e.g., baclofen), glutamate antagonists (e.g., sabeluzole), or gaseous respiration stimulants such as carbon dioxide.

Examples of Pharmaceutical Compositions and Methods of Administration

Provided herein, in certain embodiments, are compositions comprising a therapeutically effective amount of an agent that modulates the activity of the carotid body (e.g., CSE inhibitors, HO-2 inhibitors, $H_2S$ donors, CO donors).

Pharmaceutical compositions are formulated using one or more physiologically acceptable carriers including excipients and auxiliaries which facilitate processing of the active compounds into preparations which are used pharmaceutically. Proper formulation is dependent upon the route of administration chosen. A summary of pharmaceutical compositions is found, for example, in Remington: The Science and Practice of Pharmacy, Nineteenth Ed (Eahston, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more agents that modulate the activity of a carotid body (e.g., CSE inhibitors, HO-2 inhibitors, $H_2S$ donors, CO donors) and a pharmaceutically acceptable diluent(s), excipient(s), or carrier(s). In addition, the agent that modulates the activity of a carotid body is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition, as used herein, refers to a mixture of an agent that modulates the activity of a carotid body with other chemical components, such as carriers, stabilizers, diluents, dispersing agents, suspending agents, thickening agents, and/or excipients. The pharmaceutical composition facilitates administration of the agent that modulates the activity of a carotid body to an organism. In practicing the methods of treatment or use provided herein, therapeutically effective amounts of an agent that modulates the activity of a carotid body are administered in a pharmaceutical composition to a mammal having a condition, disease, or disorder to be treated. Preferably, the mammal is a human. A therapeutically effective amount varies depending on the severity and stage of the condition, the age and relative health of an individual, the potency of an agent that modulates the activity of a carotid body used and other factors. The agent that modulates the activity of a carotid body is optionally used singly or in combination with one or more therapeutic agents as components of mixtures.

The pharmaceutical formulations described herein are optionally administered to an individual by multiple administration routes, including but not limited to, oral (solid or liquid formulations), intramuscular, dermal, topical, subcutaneous, parenteral or intravenous administration routes. In specific embodiments, the pharmaceutical formulations described herein are optionally administered to an individual orally.

In some embodiments, pharmaceutical formulations described herein are optionally administered as controlled release (e.g., sustained release, immediate release, intermediate release, pulsed release) formulations.

The pharmaceutical compositions will include at least one agent that modulates the activity of a carotid body (e.g., CSE inhibitors, HO-2 inhibitors, $H_2S$ donors, CO donors), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these agents that modulate the activity of a carotid body having the same type of activity. In some situations, agents that modulate the activity of a carotid body exist as tautomers. All tautomers are included within the scope of the compounds presented herein. Additionally, the agents that modulate the activity of a carotid body (e.g., CSE inhibitors, HO-2 inhibitors, $H_2S$ donors, CO donors) exist in unsolvated as well as solvated forms with pharmaceutically acceptable solvents such as water, ethanol, and the like. The solvated forms of the agents that modulate the activity of a carotid body presented herein are also considered to be disclosed herein.

"Carrier materials" include any commonly used excipients in pharmaceutics and should be selected on the basis of compatibility with compounds disclosed herein, such as, an agent that modulates the activity of a carotid body (e.g., CSE inhibitors, HO-2 inhibitors, $H_2S$ donors, CO donors), and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Moreover, the pharmaceutical compositions described herein, which include agents that modulate the activity of a carotid body (e.g., CSE inhibitors, HO-2 inhibitors, $H_2S$ donors, CO donors), are formulated into any suitable dosage form, including but not limited to, aqueous oral dispersions, liquids, gels, syrups, elixirs, slurries, suspensions, powders suitable for reconstitution, and the like. For oral ingestion by a patient to be treated, dosage forms include and are not limited to effervescent formulations, lyophilized formulations, tablets, powders, pills, dragees, pills, capsules, solutions, gels, syrups, elixirs, suspensions or the like. In some embodiments, a formulation comprising an agent that modulates the activity of a carotid body is a solid drug dispersion. A solid dispersion is a dispersion of one or more active ingredients in an inert carrier or matrix at solid state prepared by the melting (or fusion), solvent, or melting-solvent methods. (Chiou and Riegelman, Journal of Pharmaceutical Sciences, 60, 1281 (1971)). The dispersion of one or more active agents in a solid diluent is achieved without mechanical mixing. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into oral powders for reconstitution. Solubility of an SDD comprising a drug is higher than the solubility of a crystalline form of a drug or a non-SDD amorphous form of a drug. In some embodiments of the methods described herein, an agent that modulates the activity of a carotid body is administered as SDD constituted into appropriate dosage forms described herein.

Pharmaceutical preparations for oral use are optionally obtained by mixing one or more solid excipient with an agent that modulates the activity of a carotid body (e.g., CSE inhibitors, HO-2 inhibitors, $H_2S$ donors, CO donors), optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate.

Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, or granules. In other embodiments, the pharmaceutical formulation is in the form of a powder. In still other embodiments, the pharmaceutical formulation is in the form of a tablet. Additionally, pharmaceutical formulations of an agent that modulates the activity of a carotid body are optionally administered as a single capsule or in multiple capsule dosage form. In some embodiments, the pharmaceutical formulation is administered in two, or three, or four, capsules or tablets.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to an agent that modulates the activity of a carotid body, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that comprise an agent that modulates the activity of a carotid body (e.g., CSE inhibitors, HO-2 inhibitors, $H_2S$ donors, CO donors) include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. Buccal drug delivery avoids the disadvantages encountered with oral drug administration, e.g., slow absorption, degradation of the active agent by fluids present in the gastrointestinal tract and/or first-pass inactivation in the liver. The bioerodible (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels formulated in a conventional manner.

For intravenous injections, an agent that modulates the activity of a carotid body (e.g., CSE inhibitors, HO-2 inhibitors, $H_2S$ donors, CO donors) is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Combination Formulations and Kits

In one aspect, contemplated within the scope of formulations described herein are single-pill co-formulations comprising (i) an agent that modulates the activity of the carotid body and (ii) an agent selected from carbonic anhydrase inhibitors, cholinesterase inhibitors, adenosine inhibitors, progestational agents, opiod antagonists, central nervous system stimulants, selective serotonin reuptake inhibitors (SSRIs), antidepressants, antihypertensives, calcium channel antagonists, ACE inhibitors, respiratory stimulants, alpha-2 adrenergic agonists, gamma aminobutyric acid agonists, and glutamate antagonists. In some embodiments, the two active agents in a single pill formulation have the same rate of release. In some embodiments, the two active agents in a single pill formulation each independently have a titrated dosage such that maximal therapeutic benefit is achieved by the combination treatment. In some embodiments, the two active agents in a single pill formulation each independently have a different rate of release, e.g., one agent undergoes immediate release and the second agent is released via controlled release over a period of time.

Also provided herein are kits that comprise formulations for combination therapy as described herein. The disclosure also provides kits for preventing, treating or ameliorating the symptoms of a Sleep Related Breathing Disorder in a mammal. Such kits generally will comprise one or more of the active agent as disclosed herein, and instructions for using the kit.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

In certain embodiments, the pharmaceutical compositions are presented in a pack or dispenser device which contains one or more unit dosage forms containing a compound or combination of active agents provided herein. In another embodiment, the pack for example contains metal or plastic foil, such as a blister pack.

Examples of Methods of Dosing and Treatment Regimens

The agent that modulates the activity of a carotid body (e.g., CSE inhibitors, HO-2 inhibitors, $H_2S$ donors, CO donors) is optionally used in the preparation of medicaments for the prophylactic and/or therapeutic treatment of a condition that would benefit, at least in part, from amelioration of symptoms. In addition, a method for treating any of the diseases or conditions described herein in a individual in need of such treatment, involves administration of pharmaceutical compositions containing at least one agent that modulates the activity of a carotid body described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

In the case wherein the patient's condition does not improve, upon the doctor's discretion the agent that modulates the activity of a carotid body is optionally administered chronically, that is, for an extended period of time, including throughout the duration of the patient's life in order to ameliorate or otherwise control or limit the symptoms of the patient's disease or condition.

In certain embodiments, the administered dose of an agent that modulates the activity of a carotid body (e.g., CSE inhibitors, HO-2 inhibitors, $H_2S$ donors, CO donors) is determined via a step-wise dose escalation wherein a patient's response to an agent that modulates the activity of a carotid body is titrated to determine the optimal dose for each individual patient. The titration is optionally carried out under observation in a sleep clinic and the dose is modified till the desired therapeutic effect is achieved. Measures found in polysomnography reports include the fraction of sleep time spent at each level of oxygen saturation (i.e., the percent time below an oxygen saturation of 90 percent) and/or the mean oxygen saturation. The former quantifies the cumulative exposure to hypoxemia, while the latter may be inversely associated with risk for cardiovascular disease and/or glucose intolerance and/or insulin sensitivity.

In some embodiments, as a patient is started on a regimen of an agent that modulates the activity of a carotid body (e.g., CSE inhibitors, HO-2 inhibitors, $H_2S$ donors, CO donors), the patient is also weaned off (e.g., step-wise decrease in dose) any other medication such as a respiratory stimulant, a sleep medication or the like.

In certain embodiments, the daily administered dose of an agent that modulates the activity of a carotid body (e.g., CSE inhibitors, HO-2 inhibitors, $H_2S$ donors, CO donors) is a dose such that there are no side-effects that would otherwise occur at a higher dose of the agent that modulates the activity of a carotid body. Thus, in some embodiments, administration of an agent that modulates the activity of a carotid body reduces or prevents occurrence of side-effects such as hemorrhagic shock, edema, myocardial infarction, stroke, inflammatory mononuclear cell infiltration, sepsis and/or metabolic inhibition even after long term and/or chronic usage of the agent that modulates the activity of a carotid body. In some embodiments, the administered dose of an agent that modulates the activity of the carotid body (e.g., CSE inhibitors, HO-2 inhibitors, $H_2S$ donors, CO donors) is a dose that regulates breathing during REM and/or NREM sleep.

In the case wherein the patient's status does improve, upon the doctor's discretion the administration of the agent that modulates the activity of a carotid body (e.g., CSE inhibitors, HO-2 inhibitors, $H_2S$ donors, CO donors) is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the pharmaceutical compositions described herein are in unit dosage forms suitable for single administration of precise dosages. In unit dosage form, the formulation is divided into unit doses containing appropriate quantities of one or more agents that modulate the activity of a carotid body. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The daily dosages appropriate for the agent that modulates the activity of a carotid body (e.g., CSE inhibitors, HO-2 inhibitors, $H_2S$ donors, CO donors) are from about 0.001 to 2.5 mg/kg per body weight. An indicated daily dosage in the larger mammal, including, but not limited to, humans, is in the range from about 0.1 mg to about 1000 mg, conveniently administered in divided doses, including, but not limited to, up to four times a day or in extended release form. Suitable unit dosage forms for oral administration include from about 1 to 500 mg active ingredient, from about 1 to 250 mg of active ingredient, or from about 1 to about 100 mg active ingredient. The foregoing ranges are merely suggestive, as the number of variables in regard to an individual treatment regime is large, and considerable excursions from these recommended values are not uncommon. Such dosages are optionally altered depending on a number of variables, not limited to the activity of the agent that modulates the activity of a carotid body used (e.g., CSE inhibitors, HO-2 inhibitors, $H_2S$ donors, CO donors), the disease or condition to be treated, the mode of administration, the requirements of an individual, the severity of the disease or condition being treated, and the judgment of the practitioner.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. Agents that modulate the activity of a carotid body that exhibit high therapeutic indices are preferred. The data obtained from cell culture assays and animal studies is optionally used in formulating a range of dosage for use in human. The dosage of such agents that modulate the activity of a carotid body lies preferably within a range of circulating concentrations that include the ED50 with minimal toxicity. The dosage optionally varies within this range depending upon the dosage form employed and the route of administration utilized.

Assays for Identification of Agents that Modulate Carotid Body Activity

In some embodiments, agents that modulate the activity of carotid body (e.g., CSE inhibitors, HO-2 inhibitors, $H_2S$ donors, CO donors) are identified by use of in vitro assays. By way of example, an in vitro assay for HO-2 enzyme activity is described in Kinobe et al. in *J. Pharmacol. Expt. Ther.* 2007, 323, 763-770 which assay is incorporated herein by reference. By way of example, an in vitro assay for CSE enzyme activity is described in Zhong et al. *Chinese Medical Journal,* 2009, 122, 326-330. In some embodiments, in vitro enzyme assays are adapted for high-throughput screening (HTS) using any suitable method.

In some embodiments, in vivo assays are used to determine the effect of an agent that modulates the activity of the carotid body (e.g., CSE inhibitors, HO-2 inhibitors, $H_2S$ donors, CO donors). In some embodiments, an in vivo assay for identifying a CSE inhibitor comprises (a) preparing carotid body homogenates from a test animal that has been administered a test compound; and (b) calculating $H_2S$ concentration based on absorbance; wherein a decrease in $H_2S$ concentration indicates that the test compound is a CSE inhibitor. In some embodiments of the aforementioned assay, the test animal is subjected to normoxia, acute hypoxia, chronic intermittent hypoxia, hypercapnia, or a combination thereof. Optional intermediate steps include:

effecting enzymatic reaction on L-cysteine;

quenching the enzymatic reaction with zinc acetate and trichloroacetic acid;

reacting the zinc sulfide with acidic N,N-dimethyl-p-phenylendiamine sulfate and ferric chloride; and measuring the absorbance of the assay mixture with a micro-plate reader.

In some embodiments, an in vivo assay for identifying a CSE inhibitor comprises (a) isolating carotid bodies along with carotid sinus nerves from a test animal that has been administered a test compound;

(b) challenging the carotid bodies in the recording chamber by perfusing the recording chamber with varying levels of oxygen and/or carbon dioxide; and (c) recording action potentials of the nerve bundles; wherein a decrease in action potential indicates that the test compound is a CSE inhibitor. In some embodiments of the aforementioned assay, the test animal is subjected to normoxia, acute hypoxia, chronic intermittent hypoxia, hypercapnia, or a combination thereof. Optional intermediate steps include:

placing the carotid bodies along with carotid sinus nerves in a recording chamber superfused with warm physiological saline.

Optional instruments for recording action potentials of the nerve bundles include: a suction electrode on a PowerLab/8P machine.

In some embodiments, an in vivo assay for identifying a HO-2 inhibitor comprises (a) isolating carotid bodies along with carotid sinus nerves from a test animal that has been administered a test compound;

(b) challenging the carotid bodies in the recording chamber by perfusing the recording chamber with varying levels of oxygen; and (c) recording action potentials of the nerve bundles; wherein an increase in action potential indicates that the test compound is a HO-2 inhibitor. In some embodiments of the aforementioned assay, the test animal is subjected to normoxia, acute hypoxia, chronic intermittent hypoxia, hypercapnia, or a combination thereof. In some embodiments of the aforementioned assays, the test animal is a rat or a mouse. In some embodiments, the control animal is a knock out animal (e.g., a $CSE^{-/-}$ mouse). Optional intermediate steps include:

placing the carotid bodies along with carotid sinus nerves in a recording chamber superfused with warm physiological saline.

Optional instruments for recording action potentials of the nerve bundles include: a suction electrode on a PowerLab/8P machine.

EXAMPLES

Preparation of Animals

Experiments were approved by the Institutional Animal Care and Use Committee of the University of Chicago and were performed on age matched, male wild type ($CSE^{+/+}$) and $CSE^{-/-}$ mice (2-3 months old) and male Sprague-Dawley rats (2-3 months old) except otherwise noted. In the experiments requiring sedation, animals were anaesthetized with intraperitoneal injections of urethane (1.2 g/kg, Sigma). Supplemental doses, 10% of the initial dose, of urethane were given when corneal reflexes and responses to toe pinch persisted. Animals were allowed to breathe spontaneously. Core body temperature was monitored by a rectal thermistor probe and maintained at 37±1° C. by a heating pad. At the end of the experiment, animals were euthanized by intracardiac injection (0.1 ml) of euthanasia solution (Beuthanasia-D Special, Schering-Plough, Kenilworth, N.J., USA).

Immunohistochemistry.

Carotid bodies and adrenal glands were harvested from anesthetized rats or mice (Urethane 1.2 g/kg, IP) perfused with heparinized saline followed by 4% paraformaldehyde. The protocols for fixation of carotid bodies and adrenal glands were essentially the same as described previously (Prabhakar, N. R., et al., *PNAS,* 1995, 92, 1994-7; Kline, D. D., et al., *PNAS,* 2002, 99, 821-6). For assessing CSE immunoreactivity, sections (8 micron thick) were incubated at room temperature for 2 h with polyclonal rabbit anti-CSE antibody (1:400), this antibody was raised using bacterially purified full length His-tagged CSE as antigen, and monoclonal mouse anti-tyrosine hydroxylase (1:2000, Sigma, USA), an established marker of glomus and chromaffin cells (Nurse, C. A., et. al., *Microsc Res Tech,* 2002, 59, 249-55; 2002), followed by Texas Red conjugated goat anti-rabbit IgG and FITC conjugated goat anti-mouse IgG (1:250, Molecular Probes, Oregon, USA) in PBS with 1% normal goat serum and 0.2% Triton X-100. After washing with PBS, sections were mounted in DAPI-containing media and visualized using a fluorescent microscope (Eclipse E600, Nikon).

Carotid Body Sensory Activity.

Sensory activity from carotid bodies ex vivo was recorded as previously described (Peng, Y. J., et al., *PNAS*, 2003, 100, 10073-78; Peng Y. J., et. al., *J. Physiol.*, 2006, 577, 705-716). Briefly, carotid bodies along with the sinus nerves were harvested from anaesthetized mice or rats, placed in a recording chamber (volume, 250 µl) and superfused with warm physiological saline (35° C.) at a rate of 2.5 ml/min having the following composition (mM): NaCl (140), KCl (5.4), $CaCl_2$ (2.5), $MgCl_2$ (0.5), HEPES (5.5), $_D$-glucose (11), sucrose (5), and the solution was bubbled with 100% $O_2$ and pH was adjusted to 7.35. Carotid bodies were challenged with graded hypoxia by switching the perfusate equilibrated with gas mixtures containing varying levels of $O_2$. For assessing the carotid body response to $CO_2$, bicarbonate-buffered medium equilibrated with either 90% 02+5% $CO_2$ (baseline) or 90% 02+10% $CO_2$ balance $N_2$. Clearly identifiable action potentials (2-3 active units) were recorded from one of the nerve bundles with a suction electrode and stored in a computer via a data acquisition system (PowerLab/8P, AD Instruments Pty Ltd, Australia). 'Single' units were selected based on the height and duration of the individual action potentials using a spike discrimination program (Spike Histogram Program, Power Laboratory, AD Instruments). In each carotid body, at least two chemoreceptor units were analyzed. The $P_{O2}$ and $P_{CO2}$ of the superfusion medium were determined by a blood gas analyzer (ABL 5, Radiometer, Copenhagen, Denmark).

Measurements of Respiratory Variables.

Ventilation was monitored by whole body plethysmograph, and $O_2$ consumption and $CO_2$ production were determined by the open-circuit method in unsedated mice as described previously (Peng Y. J., et. al., *J. Physiol.*, 2006, 577, 705-716). Ventilation was recorded while the mice breathed 21% or 12% $O_2$-balance $N_2$. Each gas challenge was given for 5 min $O_2$ consumption and $CO_2$ production were measured at the end of each 5 min challenge. For determining ventilatory response to $CO_2$, baseline ventilation was determined while mice breathed 21% $O_2$ followed by hypercapnic challenge with 5% $CO_2$-21% $O_2$-balance $N_2$. Sighs, sniffs, and movement-induced changes in breathing were monitored and excluded in the analysis. All recordings were made at an ambient temperature of 25±1° C.

Measurements of $H_2S$ Levels.

$H_2S$ levels in the carotid body were assayed as follows. Briefly, carotid bodies were pooled (4 carotid bodies per experiment in rats; 6 carotid bodies per experiment in mice) and tissue homogenates were prepared in 100 mM potassium phosphate buffer, pH 7.4. The enzyme reaction was carried out in sealed tubes flushed with either $N_2$ or different levels of $O_2$—$N_2$ gas mixtures. The $P_{O2}$ of the reaction medium was determined by blood gas analyzer (ABL5). The assay mixture in a total volume of 500 µl contains (in final concentration): L-cysteine, (800 µM); pyridoxal 5'-phosphate, (80 µM); potassium phosphate buffer, pH 7.4, (100 mM); and tissue homogenate (2 µg protein). The reaction mixture was incubated at 37° C. for 1 h and at the end of the reaction, alkaline zinc acetate (1% w/v; 250 up and trichloroacetic acid (10% v/v) was added sequentially to trap $H_2S$ generated and to stop the reaction, respectively. The zinc sulfide formed was reacted sequentially with acidic N,N-dimethyl-p-phenylenediamine sulfate (20 µM) and ferric chloride (30 µM) and the absorbance was measured at 670 nm using a micro-plate reader. A standard curve relating the concentration of $Na_2S$ and absorbance was used to calculate $H_2S$ concentration and expressed as nanomoles of $H_2S$ formed per hour per milligram protein.

Measurements of Catecholamine Secretion from Chromaffin Cells.

The protocols for preparation of chromaffin cells and measurements of catecholamine secretion by amperometry are as follows. Briefly, adrenal glands were harvested from anesthetized mice and rats aged P10. Chromaffin cells were enzymatically dissociated, plated on collagen (type VII; Sigma) coated coverslips, and maintained at 37° C. in a 5% $CO_2$ incubator for 12-24 h. The growth medium consisted of F-12 K medium (Invitrogen) supplemented with 10% horse serum, 5% fetal bovine serum, and 1% Penicillin/streptomycin/glutamine cocktail (Invitrogen). Catecholamine secretion from chromaffin cells was monitored by amperometry using carbon fiber electrodes. Amperometric recordings were made from adherent cells that were superfused (flow rate of about 1.0 ml/min: chamber volume ~80 µl) with a medium having the following composition (mM): 1.26 $CaCl_2$, 0.49 $M_gCl_2.6H_2O$, 0.4 $MgSO_4.7H_2O$, 5.33 KCl, 0.441 $KH_2PO_4$, 137.93, NaCl, 0.34 $Na_2HPO_4.7H_2O$, 5.56 Dextrose, and 20 HEPES at pH 7.35 and 300 mOsm. Normoxic solutions were equilibrated with room air ($P_{O2}$~146 mmHg), and hypoxic solutions were equilibrated with appropriate gas mixtures that yielded medium $PO_2$, of ~30-40 mmHg as measured by blood gas analyzer.

Drugs.

Rats and mice were treated with DL-propargylglycine (Sigma; 200 mg/kg) or Cr(III) Mesoporphyrin IX chloride (CrM459, Frontier Scientific, Logan, Utah; 1 mg/kg) intraperitoneally 2-3 h before acute experiments on anesthetized animals. NaHS (Sigma chemicals, MO) was given acutely to the ex vivo carotid body preparation. In the in vitro assays for $H_2S$ measurements, known concentrations of HO-2 inhibitor and CO donor (tricarbonyldichlororuthenium, [Ru $(CO)_3Cl_2]_2$, Sigma, USA) were added to cell lysates. All solutions with drugs were prepared fresh during the experiments.

Data Analysis.

In unsedated mice RR (breaths/min), $V_T$ (µl), minute ventilation [$V_E$ (ml/min)=RR×$V_T$], $O_2$ consumption ($V_{O2}$, ml/min), and $CO_2$ production ($V_{CO2}$ ml/min) were analyzed. Respiratory variables (RR and $V_T$) were averaged for at least 20 consecutive breaths over 5 min of inspired $O_2$ and $CO_2$ challenge. $V_T$, $V_E$, $V_{O2}$ and $V_{CO2}$ were normalized to body weight. Carotid body sensory activity (discharge from 'single' units) was averaged during 3 min of baseline and during the 3 min of gas challenge and expressed as impulses per second unless otherwise stated. The number of secretory events and the amount of catecholamine secreted per secretory event were analyzed in each experiment and the data were expressed as total catecholamines secreted. Average data are presented as mean±S.E.M. Statistical significance was assessed by either ANOVA or two-way ANOVA with repeated measures followed by Tukey's test. p values <0.05 were considered significant.

Example 1

Loss of Carotid Body Response to Hypoxia in $CSE^{-/-}$ Mice

Figure 9:
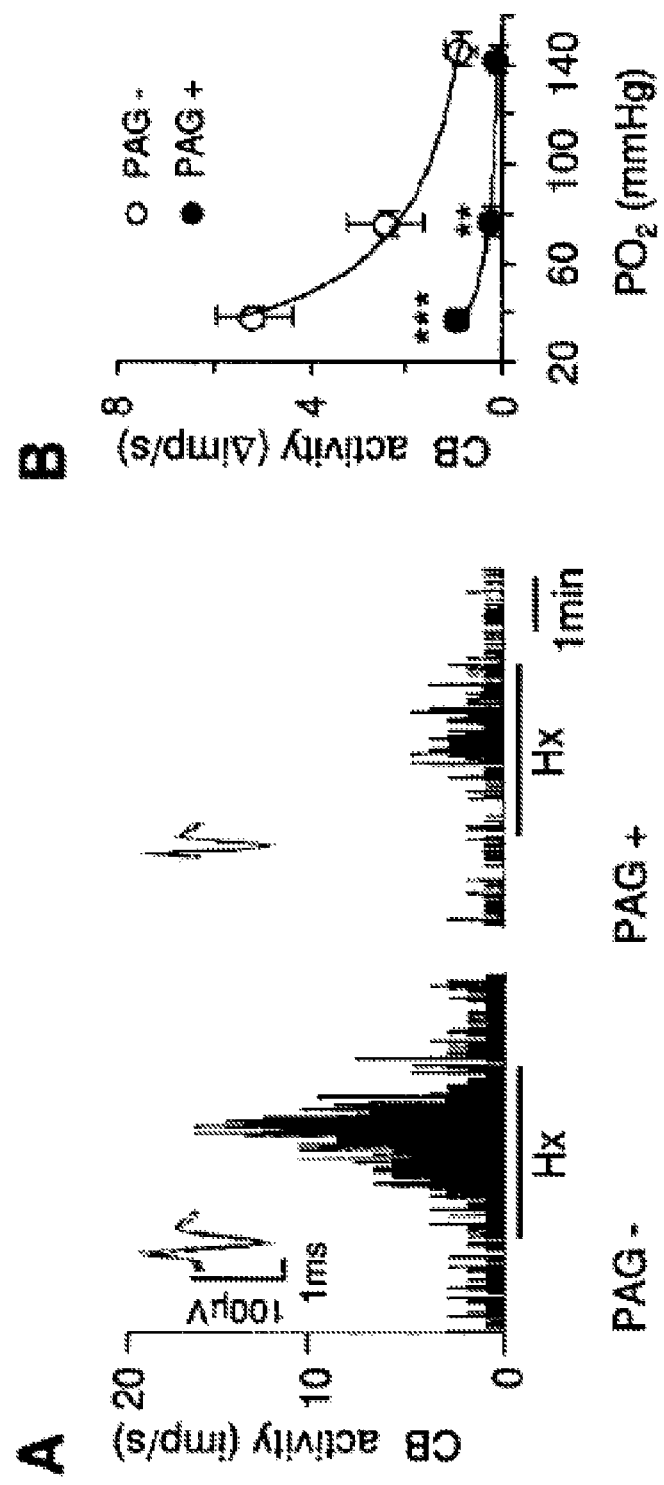
FIG. 9. (A). Illustrates carotid body response to hypoxia (Hx; $P_{O2}$=41 mmHg; at black bar) in vehicle (PAG−) and DL-propargylglycine (PAG+) treated CSE mice. Integrated carotid body sensory activity (CB activity) is presented as impulses per second (imp/s). Superimposed action potentials from the "single" fiber are presented in the inset. (B). Average data of the carotid body response to graded hypoxia. Data are presented as mean±SEM from 6 control (PAG−; n=10 fibers) and 7 PAG treated mice (PAG+; n=12 fibers). ** denote p<0.01 compared to vehicle treated mice.

CSE immunoreactivity was seen in glomus cells of carotid bodies from $CSE^{+/+}$ mice as evidenced by co-localization with tyrosine hydroxylase (TH), an established marker of glomus cells. CSE expression was absent in carotid bodies from $CSE^{-/-}$ mice (FIG. 1A). To assess the impact of CSE disruption on carotid body response to hypoxia, carotid bodies were isolated from $CSE^{+/+}$ and mutant mice and "single" unit sensory discharges were recorded from the carotid sinus nerve. In CSE$^{+/+}$ hypoxia augmented the sensory activity in a stimulus-dependent manner (FIGS. 1B and C). In striking contrast, carotid bodies from CSE$^{-/-}$ mice exhibited severely impaired sensory response to hypoxia (FIGS. 1B and C). Similar loss of the hypoxic response was also seen in CSE$^{+/+}$ mice treated systemically with $_{DL}$-propargylglycine (PAG), an inhibitor of CSE (FIG. 9) (Abeles, R. H., et al., *J. Am. Chem. Soc.*, 1973, 95, 6124-6125; Washtein, W., et al., Biochemistry, 1997, 16, 2485-91). On the other hand, acute application of PAG was ineffective in preventing the hypoxic response, a finding consistent with a recent report (Li, Q., et al., *Antioxid. Redox. Signal.*, 2010 [Epub ahead of print]).

H$_2$S generation was monitored in carotid bodies from CSE$^{+/+}$ and CSE$^{-/-}$ mice under normoxia (P$_{O2}$, ~146 mmHg) and hypoxia (P$_{O2}$, ~40 mmHg). Basal H$_2$S generation under normoxia was significantly less in CSE$^{-/-}$ compared to CSE mice (CSE$^{+/+}$=55±3 vs. CSE$^{-/-}$=29±1 nmol/h/mg protein; 53% less in mutant mice). Hypoxia increased H$_2$S generation in CSE$^{+/+}$ but not in mutant mice (CSE$^{+/+}$ mice 2.5 fold increase vs. CSE$^{-/-}$ mice 0.3 fold increase; p<0.001; FIG. 1D).

To assess whether the attenuated hypoxic response in mutant mice was due to reduced excitability of the carotid body, sensory response to CO$_2$, another physiological stimulus, was determined. Carotid bodies from CSE$^{+/+}$ and CSE$^{-/-}$ mice responded to CO$_2$ with a comparable increase in sensory discharge (FIGS. 1E and F).

Example 2

Impaired Ventilatory Response to Acute Hypoxia in CSE$^{-/-}$ Mice

Figure 2:
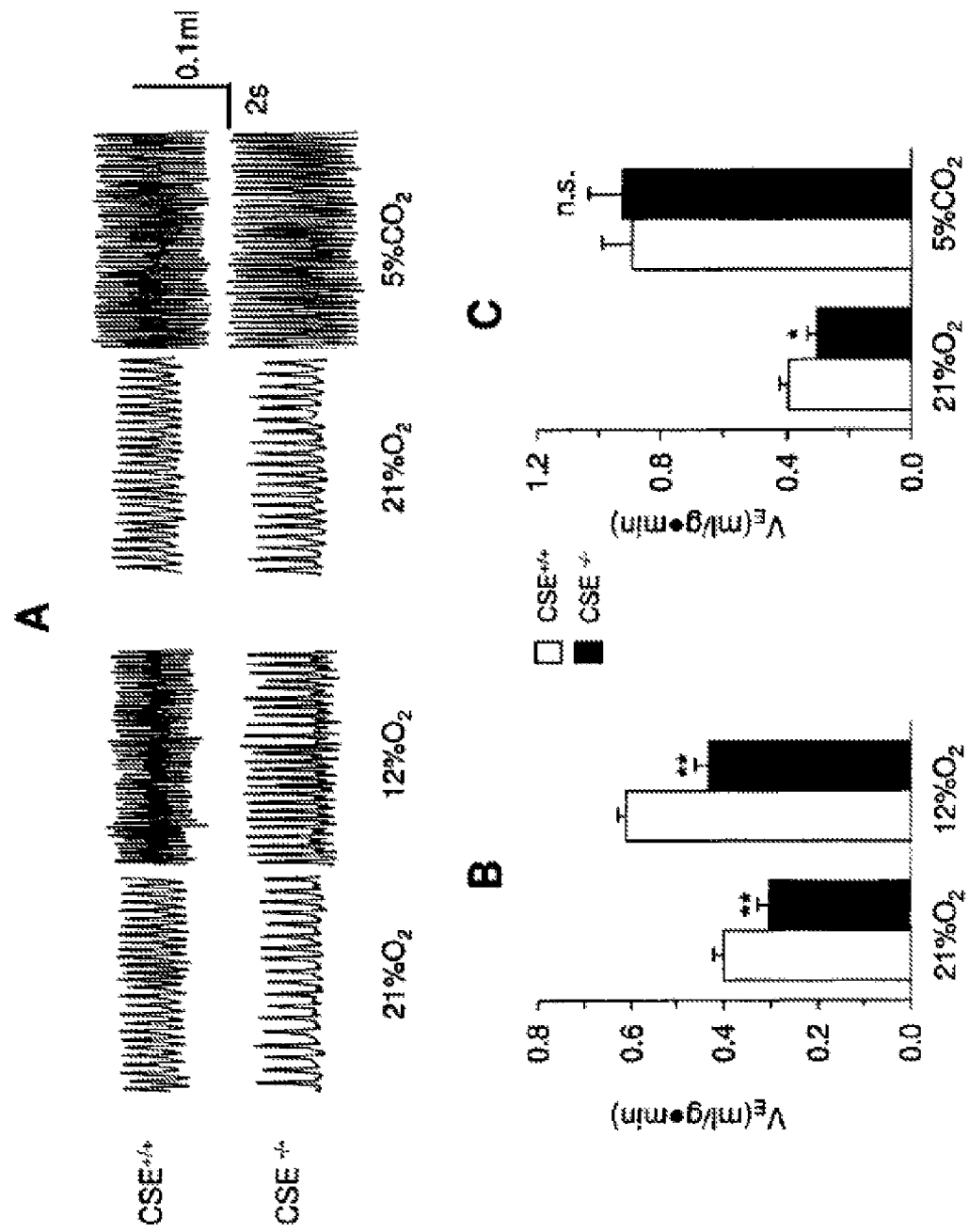
FIG. 2. Illustrates ventilatory responses to hypoxia and hypercapnia in $CSE^{+/+}$ and $CSE^{-/-}$ mice. Ventilation was measured in unsedated mice by whole body plethysmography under normoxia (21% $O_2$), hypoxia (12% $O_2$), and hypercapnia (5% $CO_2$). Hypoxia and hypercapnia lasted for 5 min. Representative tracings of breathing are shown in (A) and average data of minute ventilation ($V_E$) in response to 12% $O_2$ i.e., hypoxia (B) and hypercapnia i.e., 5% $CO_2$ (C). The data presented are mean±SEM from 8 $CSE^{+/+}$ and $CSE^{-/-}$ mice each. ** represent p<0.01 and n.s. represent p>0.05 i.e. not significant.

Ventilatory responses to 21% O$_2$ (normoxia) and 12% O$_2$ (hypoxia) were determined by whole body plethysmography in awake, non-sedated CSE$^{+/+}$ and CSE$^{-/-}$ mice. Baseline ventilation (V$_E$) was significantly less in CSE$^{-/-}$ compared to CSE$^{+/+}$ mice (FIGS. 2A and B), which was due to significantly lower respiratory rates (RR) in mutant mice (FIG. 7). More importantly, the magnitude of hypoxic ventilatory response was significantly less in CSE$^{-/-}$ compared to CSE$^{+/+}$ mice (FIGS. 2A and B); which was due to decreased stimulation of RR and tidal volume (V$_T$; FIG. 7). Changes in O$_2$ consumption (V$_{O2}$) and CO$_2$ production (V$_{CO2}$) under hypoxia, however, were comparable between mutant and CSE$^{+/+}$ mice (FIG. 7). In contrast, CSE$^{+/+}$ and CSE$^{-/-}$ mice responded to hypercapnia (5% CO$_2$) with comparable increases in V$_E$ (FIGS. 2A and C), RR, and V$_T$ (FIG. 8).

Example 3

CSE and Hypoxic Sensitivity of the Rat Carotid Body

Figure 3:
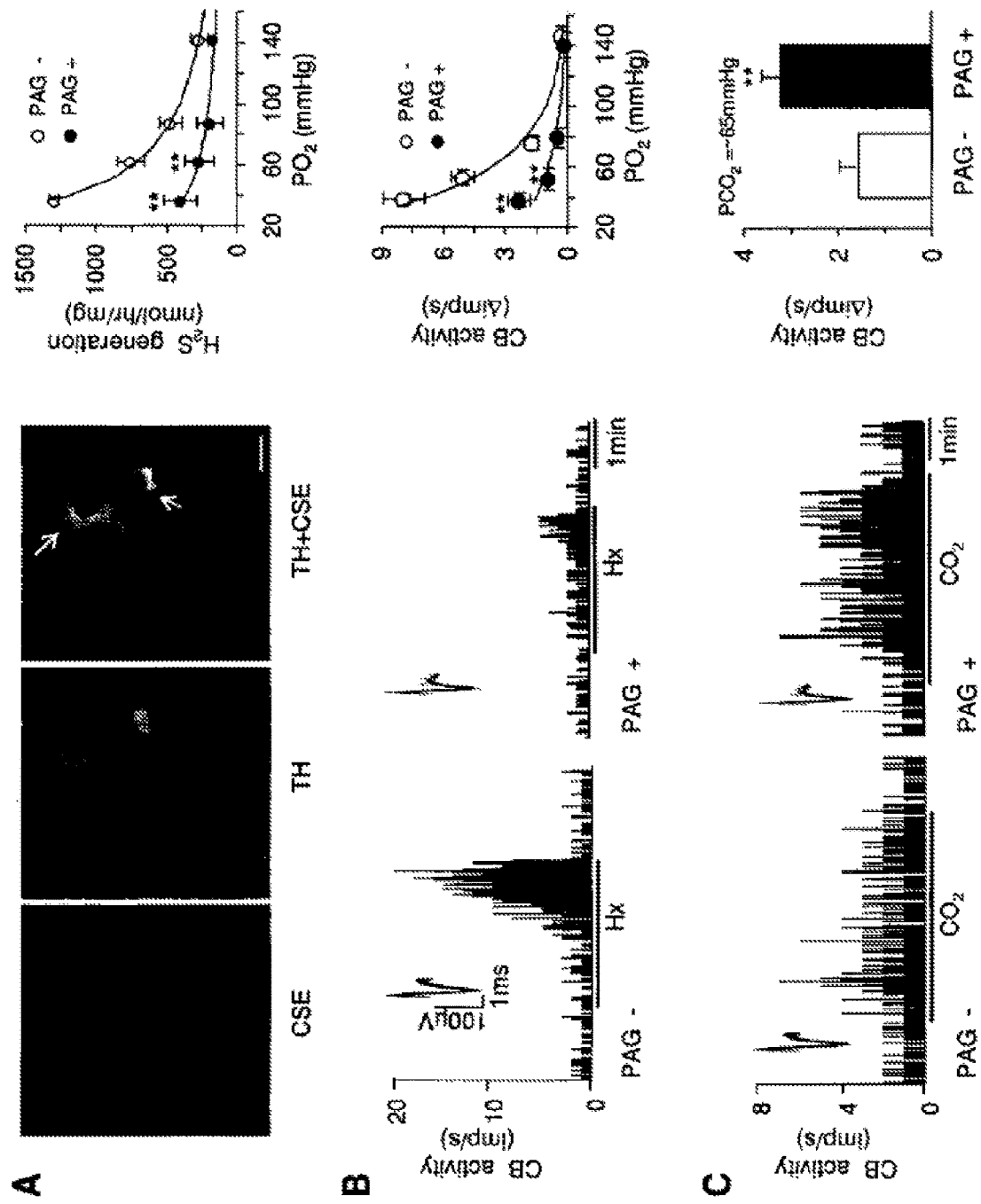
FIG. 3. (A). Illustrates cystathionine γ-lyase (CSE) expression in rat carotid body. Carotid body sections were stained with antibodies specific for CSE and tyrosine hydroxylase (TH), a marker of glomus cells (left panel). Effects of graded hypoxia on $H_2S$ levels in vehicle (PAG−) and DL-propargylglycine (PAG+) treated carotid bodies. Data are mean±SEM from 5 individual experiments (right panel). (B). Examples of carotid body response to hypoxia (at black bar; Hx; $P_{O2}$=38 mmHg) in vehicle and PAG treated rats (left panel). Average (mean±SEM) data of sensory response to graded hypoxia (right panel), PAG−n=12 fibers from 6 rats; PAG+n=10 fibers from 6 rats. (C). Example of carotid body response to $CO_2$ in the same rats as in (B) ($P_{CO2}$, 68 mmHg; at black bar; left panel) and average (mean±SEM) data of $CO_2$ response (right panel). Data derived from n=9 fibers (PAG−) and n=10 (PAG+) fibers from 6 rats each. In (B) and (C), Integrated carotid body sensory activity (CB activity) is presented as impulses per second (imp/s). Superimposed action potentials from the single fiber are presented in the inset. ** represent p<0.01.

To assess whether CSE contributes to the carotid body response to hypoxia in species other than mouse, CSE expression and the effect of its pharmacologic inhibition by PAG were determined in rat carotid bodies. CSE immunoreactivity was found in glomus cells of the rat carotid body (FIG. 3A, left panel). Rat carotid bodies being ~3 times bigger than those found in mouse (~80 μg in rat vs. 25 μg in mouse), we were able to determine the effects of graded hypoxia on H$_2$S generation. Basal H$_2$S generation in rat carotid body was 266±61 nmol/h/mg protein which was significantly higher than in mouse carotid body (55±3 nmol/h/mg protein; p<0.01). Hypoxia increased H$_2$S levels in a stimulus-dependent manner (FIG. 3A, right panel). The magnitude of hypoxia-evoked H$_2$S production was comparable in rat and mouse (~5 fold increase in rats vs. ~3.5 fold in mice at P$_{O2}$ of ~40 mmHg). In PAG treated rats, basal H$_2$S levels were reduced by 55% (vehicle=266±61 vs. PAG=147±50 nmol/h/mg protein; p<0.05) and hypoxia-evoked H$_2$S generation was nearly absent in carotid bodies (FIG. 3A, right panel).

Figure 10:
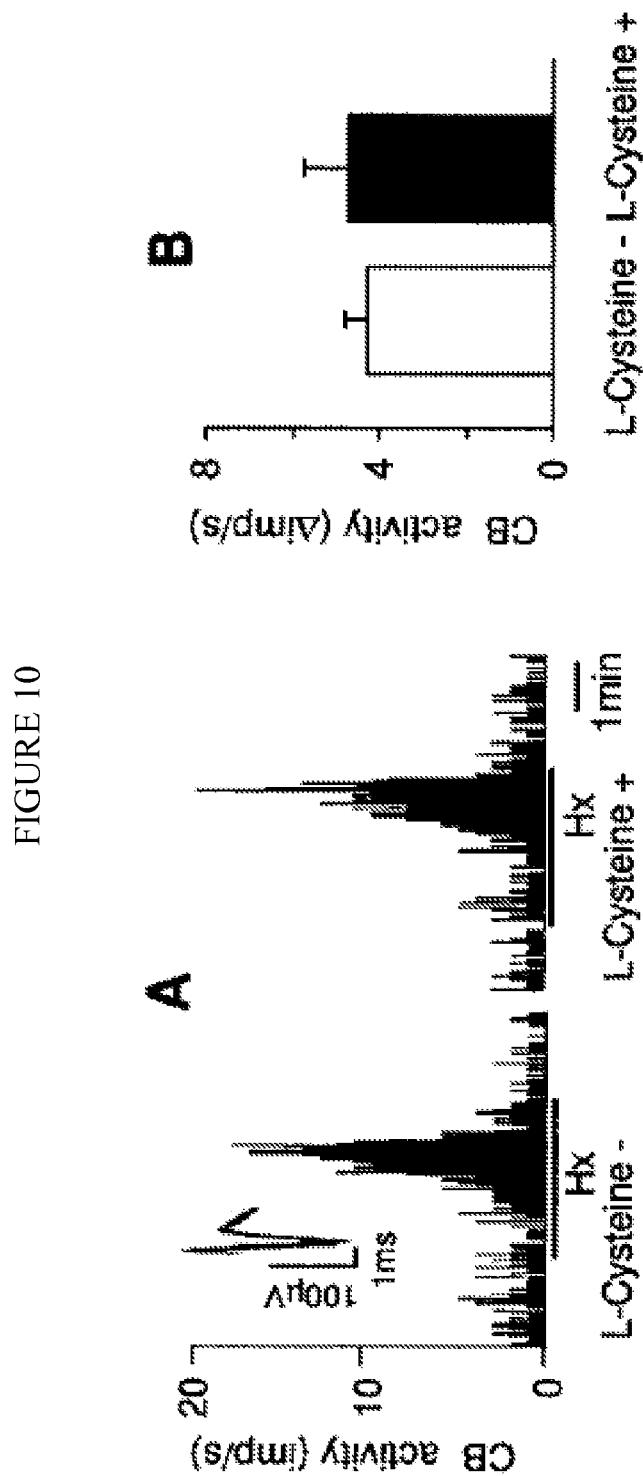
FIG. 10. (A). Illustrates isolated rat carotid body response to hypoxia (Hx; $P_{O2}$=37 mmHg; at the black bar) without (L-cysteine−) and with (L-cysteine+) 100 μM L-cysteine. Integrated carotid body sensory activity (CB activity) is presented as impulses per second (imp/s). Superimposed action potentials from the "single" fiber are presented in the inset. (B). Average data of the carotid body response to hypoxia with and without 100 μM L¬cysteine. Data are presented as mean±SEM from 6 rats (n=12 fibers). n.s. denotes p>0.05; not significant compared to without L-cysteine.

In vehicle treated rats, hypoxia augmented sensory activity in a stimulus-dependent manner, and this response was significantly attenuated in PAG treated rats (FIG. 3B). The attenuated hypoxic response in PAG treated rats could be secondary to accumulation of cysteine resulting from CSE inhibition. However, 100 μM L-cysteine had no significant effect on the hypoxic response (FIG. 10). In sharp contrast, carotid body response to CO$_2$ was significantly augmented in PAG treated rats (same rats tested for hypoxia; FIG. 3C). CSE knockouts responded in a similar fashion to wild-type mice when challenged with hypercapnia (see FIGS. 1E, 1F, and 2C). Rats given PAG demonstrated increased CB activity when challenged with hypercapnia (see FIG. 3C).

Example 4

CSE and Hypoxic Sensitivity of the Rat Carotid Body

The effect of CSE inhibitor BCA is determined using the procedure described above. An effective CSE inhibitor blunts the activity of the carotid body.

Example 5

H$_2$S Stimulates Carotid Body Sensory Activity

Figure 4:
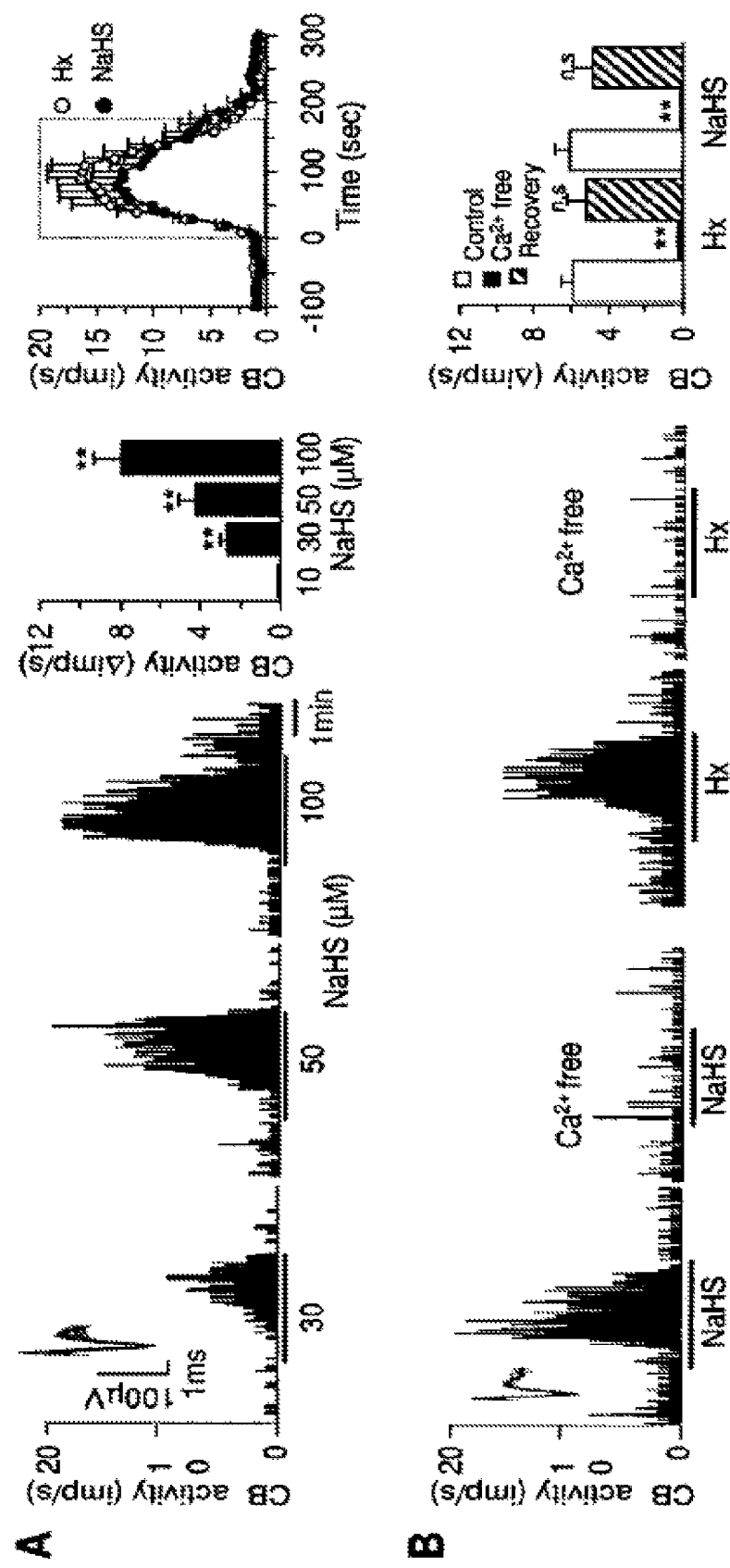
FIG. 4. (A). Illustrates an example of rat carotid body response to increasing concentrations of NaHS, a $H_2S$ donor (at black bar; left panel). Average (mean±SEM) data of dose-response to NaHS (middle panel) and time course of sensory response to NaHS (100 μM) and hypoxia ($P_{O2}$=42 mmHg; right panel). Data in middle and right panels were obtained from n=13 fibers from 6 rats. (B). Effect of $Ca^{2+}$ free medium on rat carotid body responses to 100 μM NaHS and hypoxia (Hx; $P_{O2}$=42 mmHg; at black bar). $CaCl_2$ was replaced by 3 mM $MgCl_2$ and 5 mM EGTA was added to the medium. Left panel represents an example and right panel average (mean±SEM) data from 5 rats (n=8 fibers). In (A) and (B), Integrated carotid body sensory activity (CB activity) is presented as impulses per second (imp/s). Superimposed action potentials from the single fiber are presented in the inset. ** represent p<0.01 and n.s. represent p>0.05 i.e. not significant.
Figure 11:
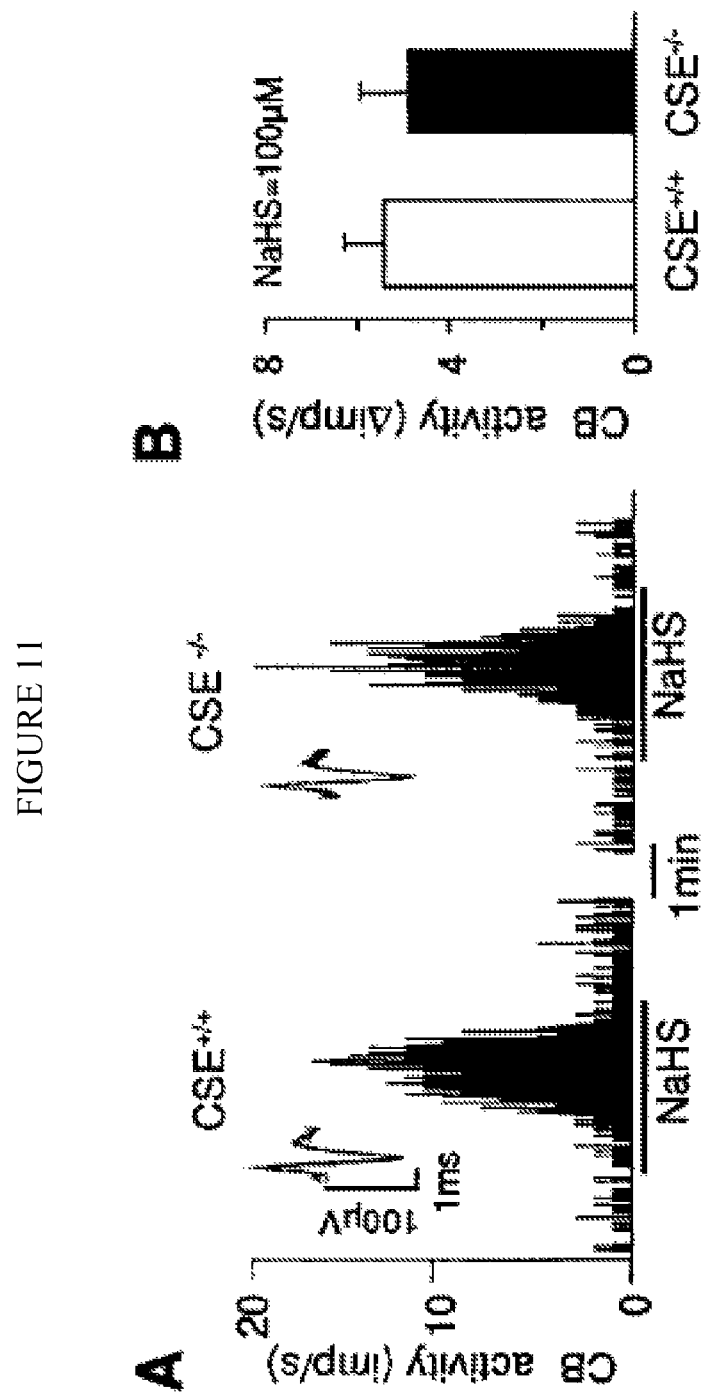
FIG. 11. (A). Illustrates isolated carotid body response to 100 μM NaHS, an $H_2S$ donor in $CSE^{+/+}$ and $CSE^{-/-}$ mice. Black bar represents the duration of NaHS application. Integrated carotid body sensory activity (CB activity) is presented as impulses per second (imp/s). Superimposed action potentials from the "single" fiber are presented in the inset. (B). Average data of the $CSE^{+/+}$ and $CSE^{-/-}$ carotid body responses to 100 μM NaHS. Data are presented as mean±SEM from 6 $CSE^{+/+}$ (n=12 fibers) and 5 $CSE^{-/-}$ mice (n=10 fibers). n.s. denotes p>0.05; not significant.

The effects of exogenous administration of H$_2$S on the sensory activity of the carotid body were examined. NaHS, an H$_2$S donor, augmented carotid body activity in rats (FIG. 4A) and in CSE CSE$^{-/-}$ mice (FIG. 11). Like hypoxia, carotid body response to NaHS was stimulus-dependent, occurred within seconds after its application, and sensory activity promptly returned to baseline after termination of the stimulus (FIG. 4A, middle and right panels).

Figure 12:
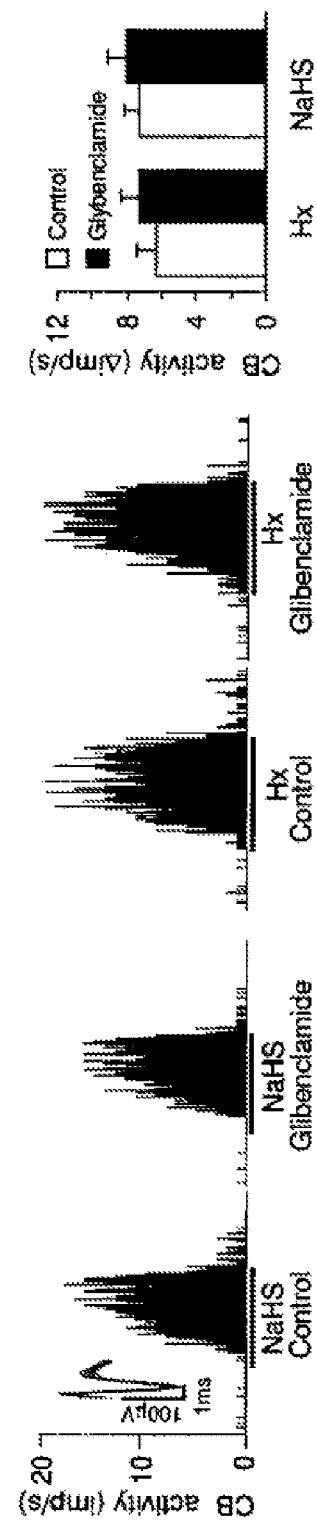
FIG. 12. Illustrates examples of rat carotid body responses to 100 μM NaHS and hypoxia (Hx; $P_{O2}$=42 mmHg; at black bars) in presence of 100 μM glibenclamide (left panel) and average data (mean±SEM) from n=8 fibers from 5 rats (right panel).

Ca$^{2+}$ influx into glomus cells is critical for carotid body response to hypoxia (Prabhakar, N. R., et. al., *J. Appl. Physiol.*, 2000, 88, 2287-95). To assess whether Ca$^{2+}$ is also important for sensory excitation by H$_2$S, carotid body responses to NaHS were examined in the presence of C$^{a2+}$-free and EGTA containing medium. Carotid body responses to NaHS as well as to hypoxia were abolished in the presence of CA$^{2+}$-free and EGTA containing medium (FIG. 4B). On the other hand, glibenclamide, a potent inhibitor of ATP-sensitive potassium (K$_{ATP}$) channels which mediate H$_2$S responses in vasculature (Zhao, W., et. al., *EMBO J.*, 2001, 20, 6008-16), failed to prevent carotid body response either to NaHS or to hypoxia (FIG. 12).

Example 6

H$_2$S Stimulates Carotid Body Sensory Activity

The following H$_2$S donor compounds are tested using the procedure described above:

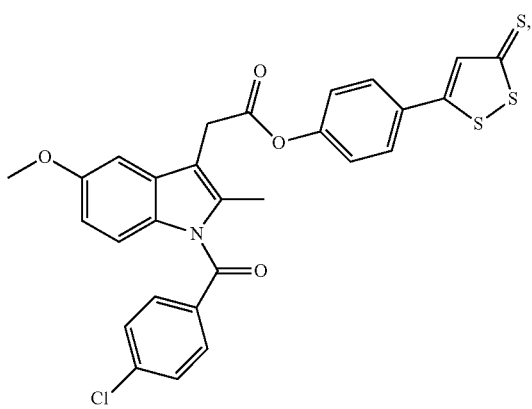

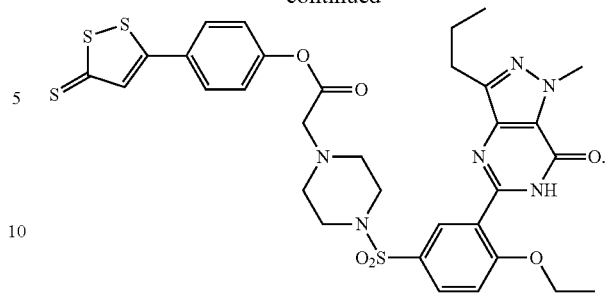

An effective H₂S donor compound augments the activity of the carotid body and/or is a respiratory stimulant.

Example 7

HO-2 Modulates H$_2$S Generation by CSE

Figure 5:
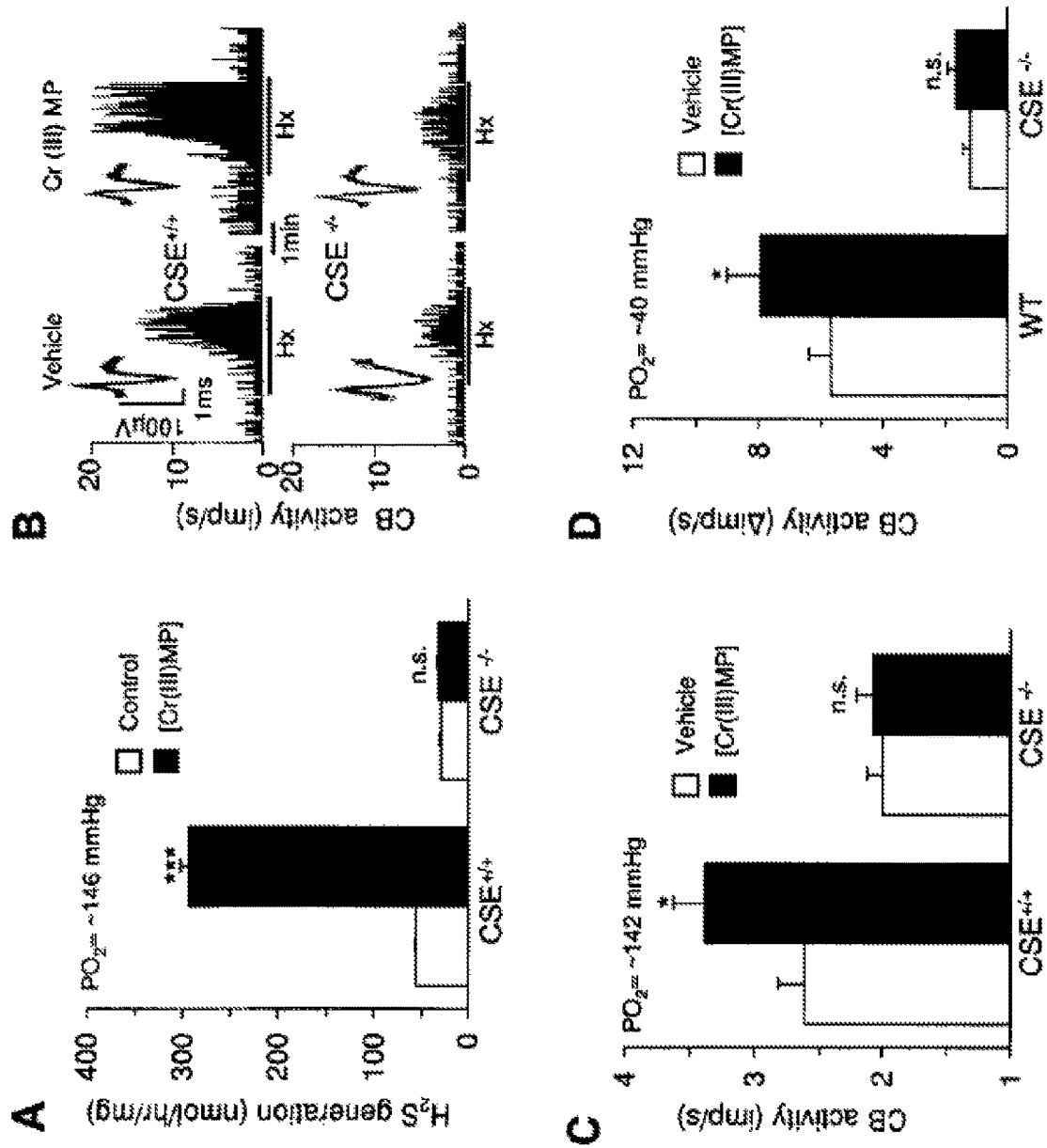
FIG. 5. (A). Illustrates effect of Cr(III)MP (1 μM), an inhibitor of heme oxygenase 2 on H2S generation in carotid bodies under normoxia ($P_{O2}$~146 mmHg) from $CSE^{+/+}$ and $CSE^{-/-}$ mice. Data presented are mean±SEM from 3 experiments. Examples of baseline and hypoxic response (Hx; $P_{O2}$~40 mmHg at black bar) of carotid bodies from vehicle and Cr(III)MP treated $CSE^{+/+}$ and $CSE^{-/-}$ mice (B) and average data (mean±SEM) from 6 mice in each group (n=8-12 fibers) in (C) and (D). In (B), Integrated carotid body sensory activity (CB activity) is presented as impulses per second (imp/s). Superimposed action potentials from the single fiber are presented in the inset. *** and * represent p<0.001 and p<0.05, respectively. n.s. represent p>0.05 i.e. not significant.
Figure 13:
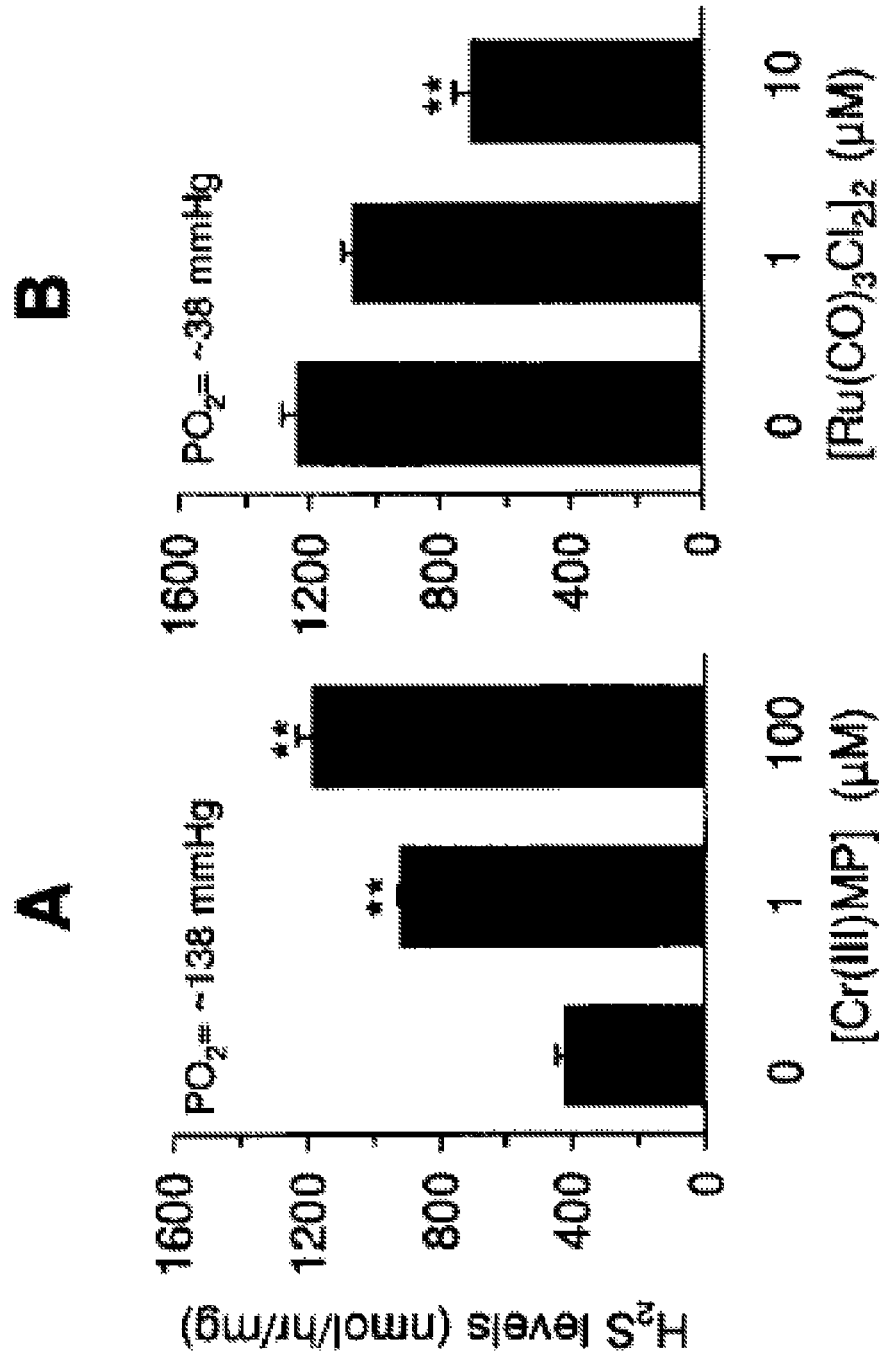
FIG. 13. Illustrates effect of Cr(III)MP, an HO-2 inhibitor and $[Ru(CO)_3Cl_2]_2$, a CO donor on $H_2S$ generation in rat carotid body. $H_2S$ levels were determined under normoxia ($P_{O2}$, =138 mmHg) in presence of 1 and 100 μM Cr(III)MP (A) and under hypoxia ($P_{O2}$=38 mmHg) in presence of 1 and 10 μM $[Ru(CO)_3Cl_2]_2$ (B). Data presented are mean±SEM from 5 experiments. ** represent p<0.01 compared to controls.
Figure 14:
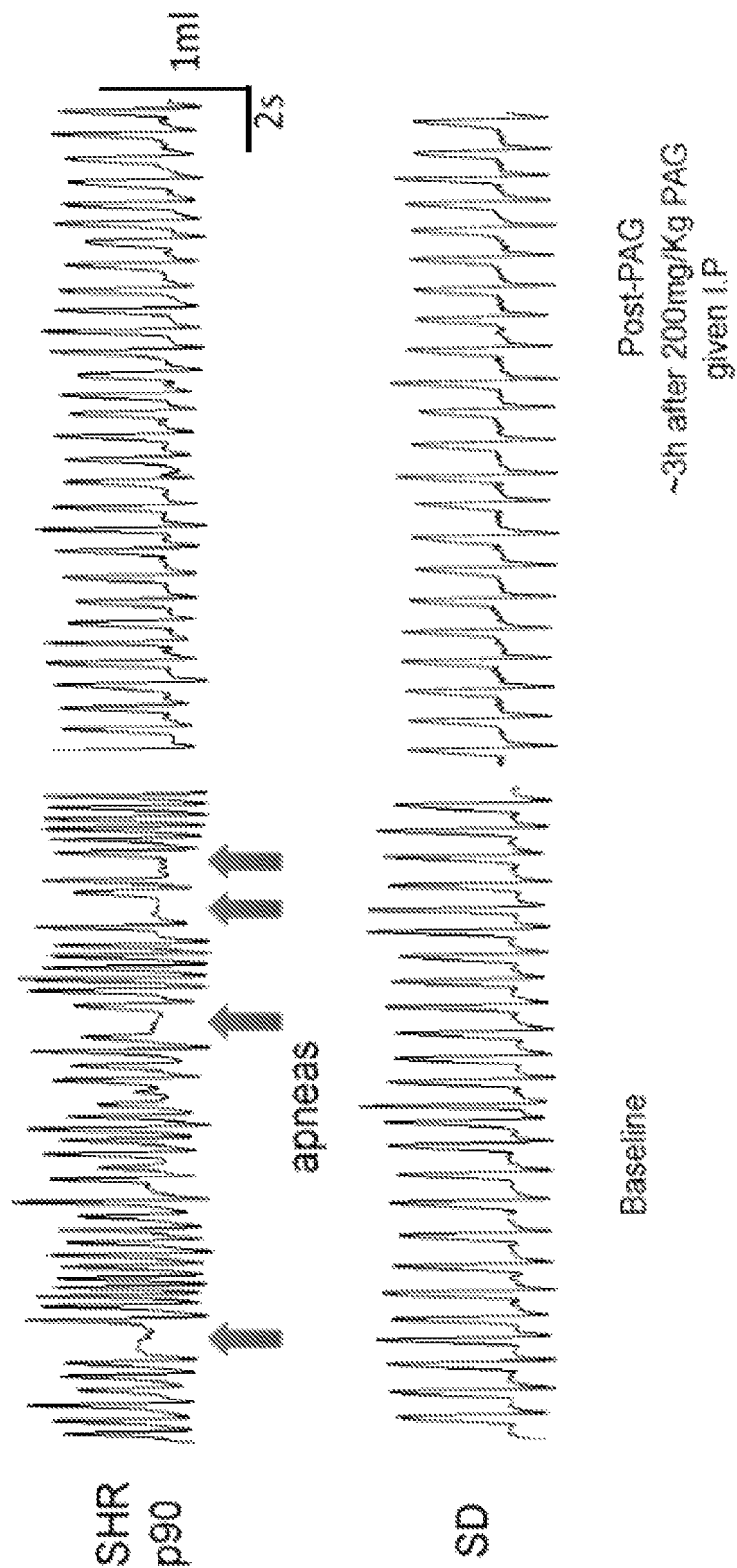
FIG. 14. Illustrates effect of a CSE inhibitor in rats. Spontaneously hypertensive rats (SHR) were treated with the CSE inhibitor propargylglycine. Their respiration was measured using whole body polysomnography. The rate and depth of respiration is shown in FIG. 14. The control animals were Sprague-Dawley rats. The PAG treatment normalized the SHR rat's breathing pattern. The effect of PAG on the control rats was small, reducing respiration frequency very slightly.

Glomus cells express HO-2, an enzyme that generates CO (Prabhakar, N. R., *PNAS*, 1995, 92, 1994-7). To assess whether the HO-2-CO system affects CSE activity, H$_2$S generation was determined in CSE$^{+/+}$ and CSE$^{-/-}$ carotid bodies in the presence and absence of Cr (III) mesoporphyrin IX chloride [Cr (III) MP], an inhibitor of HO-2 (16). As little as 1 μM Cr (III) MP increased H$_2$S generation 6 fold in CSE$^{+/+}$ mice carotid bodies under normoxia, and this response was abolished in mutant mice (FIG. 5A). Systemic administration of Cr (III) MP significantly increased baseline carotid body activity and potentiated the hypoxic response in CSE but not in mutant mice (FIG. 5B-D). In rat carotid bodies, Cr (III) MP also enhanced H$_2$S generation under normoxia, and a CO donor (tricarbonyldichlororuthenium, [Ru(CO)$_3$Cl$_2$]$_2$) inhibited H$_2$S generation by hypoxia nearly to the levels seen under normoxia (FIG. 13).

Example 8

HO-2 Modulates H$_2$S Generation by CSE

The following HO-2 inhibitors are tested using the procedure described above:

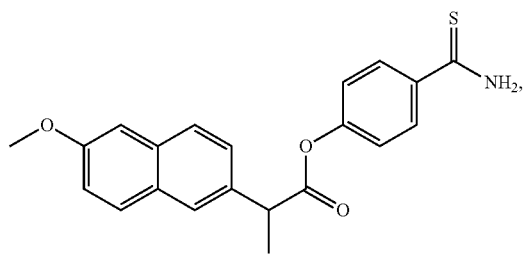

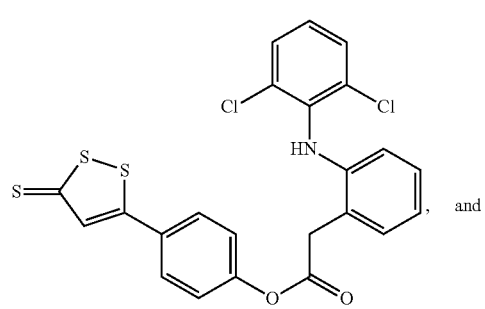

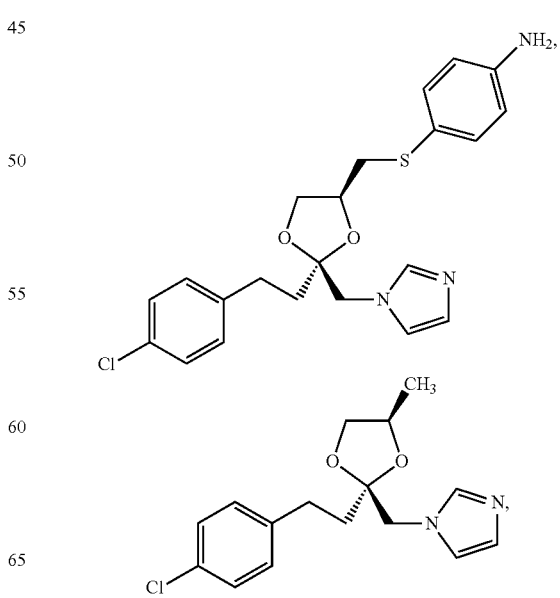

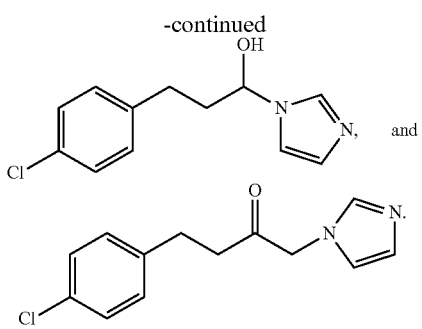

An effective HO-2 inhibitor compound augments the activity of the carotid body and/or is a respiratory stimulant.

Example 9

Effect of CO Donor Compounds

Because increased HO activity is associated with the production of carbon monoxide (CO), the effect of CO donor compound tricarbonylchloro(glycinato)ruthenium(II) [Ru(CO)$_3$Cl(glycinate)], is tested using the procedure described above to determine the effect of a CO donor compound on carotid body activity. An effective CO-donor compound blunts the activity of the carotid body.

Example 10

CSE Disruption Impairs Hypoxic Sensing by Neonatal Adrenal Medullary Chromaffin Cells (AMC)

Figure 6:
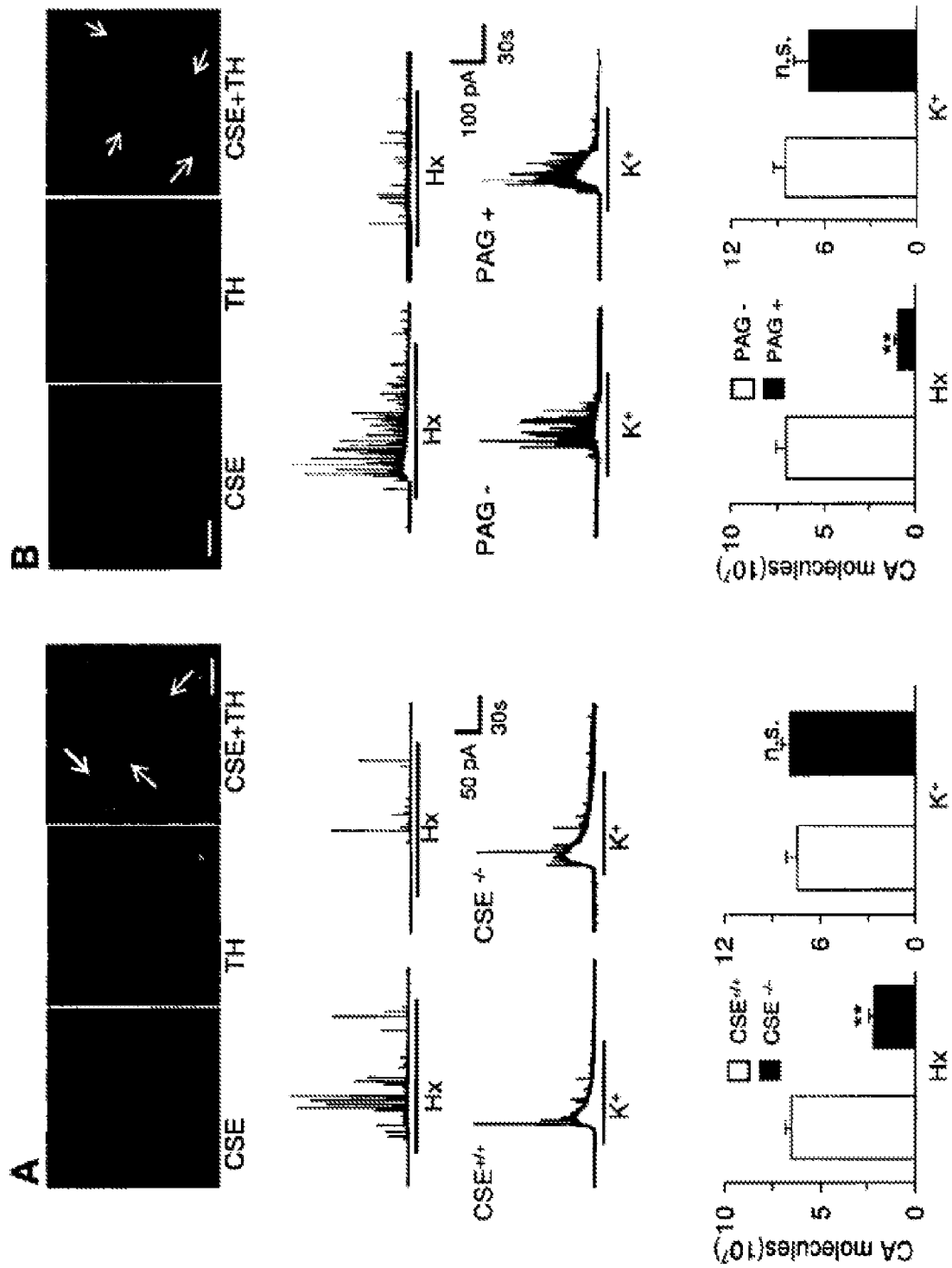
FIG. 6. Top panel: Illustrates Cystathionine γ-lyase (CSE) expression in neonatal adrenal medullary chromaffin cells (AMC) from mice (A) and rats pups (B). Middle panel: Examples of catecholamine secretion from AMC from neonatal mice (A) and rats (B) in response to hypoxia (Hx; $P_{O2}$=36 mmHg) or high $K^+$ (40 mM). Black bar represents the duration of hypoxia or $K^+$ application. Bottom panel: Average data (mean±SEM) of total catecholamine (CA) secreted during Hx or $K^+$ (CA molecules $10^7$ i.e., number of secretory events multiplied by catecholamine molecules secreted per event). n=9 cells each from $CSE^{+/+}$ and $CSE^{-/-}$ and n=10-12 cells from rat pups. ** represent p<0.01 and n.s. represent p>0.05 i.e. not significant compared to $CSE^{+/+}$ mice or vehicle treated rat cells.

Hypoxia stimulates catecholamine secretion from neonatal AMC (Souvinnakitti, D., et al., *J. Neurophysiol.*, 2009, 101, 2837-46; Thompson, R. J., et al., *J. Physiol.*, 1997, 498, 503-510). To assess the role of CSE in AMC, studies were performed on neonatal mice and rats at age P10. CSE immunoreactivity was seen in mice and rat AMC (FIGS. 6A and B, top panels) but was absent in AMC from CSE$^{-/-}$ mice (data not shown). Hypoxia-evoked catecholamine secretion was monitored by amperometry from single AMC harvested from CSE$^{-/-}$ mice and PAG treated rat pups. Control studies were performed on age matched CSE$^{+/+}$ mice and vehicle treated rat pups, respectively. In CSE$^{+/+}$ mice, hypoxia elicited robust catecholamine secretion, which was greatly reduced or absent in AMC from mutant mice (FIG. 6A, middle panel). A similar reduction in hypoxia-evoked catecholamine secretion was also seen in PAG treated rat pups (FIG. 6B, middle panel). In contrast, K$^+$-evoked (40 mM K$^+$; non-selective depolarizing stimulus) catecholamine secretion was unaffected in CSE$^{-/-}$ mice and PAG treated rat pups (FIGS. 6A and B, middle and bottom panels). H$_2$S generation increased under hypoxia in adrenal glands from CSE$^{+/+}$ mice and vehicle treated rat pups, and this response was greatly reduced or absent in CSE$^{-/-}$ mice and PAG treated rat pups respectively (data not shown).

Example 11

Oral Composition—Capsule

To prepare a pharmaceutical composition for oral delivery, 100 mg of a CSE inhibitor or an HO-2 inhibitor or an H$_2$S donor, is mixed with 750 mg of starch. The mixture is incorporated into an oral dosage unit, such as a hard gelatin capsule, which is suitable for oral administration.

Example 12

Oral Composition—Fast-Disintegrating Sublingual Tablet

A fast-disintegrating sublingual tablet is prepared by mixing 48.5% by weigh of a CSE inhibitor or an HO-2 inhibitor or an H$_2$S donor, 44.5% by weight of microcrystalline cellulose (KG-802), 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of a CSE inhibitor or an HO-2 inhibitor or an H$_2$S donor with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 13

Clinical Trial to Determine Effect of CSE Inhibitor on CSA in Patients

This is a phase II study to determine efficacy of oral PAG in treatment of central sleep apnea. 30 patients with a history of CSA and heart failure will be enrolled.

Study Type: Interventional; Study Design: Allocation: Randomized; Control: Placebo Control Endpoint Classification: Safety/Efficacy Study Intervention Model: Crossover Assignment; Masking: Double Blind (Subject, Caregiver, Investigator, Outcomes Assessor)

Eligibility: 21 Years to 79 Years; Genders Eligible for Study: Both; Accepts Healthy Volunteers: No Inclusion Criteria: New York Heart Association (NYHA) functional class II through IV heart failure due to ischemic, hypertensive, or idiopathic dilated cardiomyopathy and whose condition has been stabilized by means of optimal medical therapy for at least one month; an LVEF of less than 40 percent on radionuclide angiography; and central sleep apnea, defined as 15 or more episodes of apnea and hypopnea per hour of sleep, more than 50 percent of which are determined to be central rather than obstructive.

Exclusion Criteria: Pregnancy, myocardial infarction, unstable angina or cardiac surgery within the previous three months, and obstructive sleep apnea.

Primary Outcome Measures: Apnea Hypopnea Index measured by Respiratory Inductance Plethysmography (RIP); Central Apnea Index; Mean Oxygen Saturation for the entire night; Obstructive Apnea Index; Hypopnea Index.

Secondary Outcome Measures: Oxygen Saturation Means for Awake Sleep Stage; Oxygen Saturation Means for Non-Rapid Eye Movement Sleep Stage; Oxygen Saturation Means for Rapid Eye Movement Sleep Stage; Percentage of oxygen saturation is less than 80%; Latency to Persistent Sleep; Total Sleep Time; Awake Time after Persistent Sleep; Number of Awakenings after Persistent Sleep; Subjective Sleep Latency; Subjective Total Sleep Time; Subjective Sleep Quality; Subjective Number of Awakening; Subjective Ease of Falling Back to Sleep after Awakening; Subjective Level of Alertness; Subjective Ability to Concentrate; Percentage of Total Sleep Time in REM sleep; Percentage of Total Sleep Time in Stage 1 NREM sleep; Percentage of Total Sleep Time in Stage 2 NREM sleep; Percentage of Total Sleep Time in Stage 3/4 NREM sleep; Percentage of Total Sleep Time in latency to REM as determined by polysomnography.

Example 14

Clinical Trial to Determine Effect of HO-2 Inhibitor in Prevention of Altitude Sickness High altitude pulmonary oedema (HAPE) is a life-threatening non-cardiogenic lung injury precipitated by exaggerated pulmonary hypertension. Elevated pulmonary artery pressure (PAP) caused by hypoxic pulmonary vasoconstriction (HPV) leads to development of HAP. The present study will determine whether the use of HO-2 inhibitor causes a reduction in PAP, and/or prevents elevation in PAP.

The purpose of this study is to determine whether oral use of an HO-2 inhibitor can prevent or attenuate high altitude illnesses. A double-blind placebo-controlled randomised trial will be conducted to assess the effect of HO-inhibitor administration on PASP and Lake Louise AMS score at an altitude of 5000 m. The following compound will be tested:

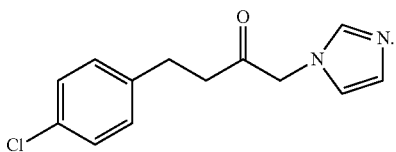 [SMILES: O=C(CCc1ccc(Cl)cc1)Cn1ccnc1]

Inclusion Criteria: Participant in a high altitude expedition.

Exclusion Criteria: Previous history of high altitude pulmonary edema.

Primary Outcome Measures: Pulmonary Artery Systolic Pressure (PASP)

Example 15

Clinical Trial to Determine Effect of CSE Inhibitor in Prevention of Cheyne-Stokes Breathing—Central Sleep Apnea The purpose of this study is to assess changes in left ventricular performance using echocardiography as well as ventricular remodeling, changes in sleep and changes in mood, anxiety and cognitive functions occurring as a result of treatment of predominant central sleep apnea. Patients having Left ventricular ejection fraction (LVEF) less than or equal to 45% by means of echocardiography, radionucleotide angiography, left ventriculography or cardiac MRI documented less than 12 weeks before randomization, with a diagnosis of sleep disordered breathing (SDB) with an apnoea-hypopnoea-index (AHI) of >15/hr with at least 50% central events and a central AHI of at least 10/hr will be enrolled in the study. At the start of study, patients should be clinically stable with no change in medication and no unplanned hospitalisation for heart failure in preceding month.

Patients in the treatment group are administered an oral formulation comprising BCA. Patients in the control group receive a placebo.

Primary Outcome Measures: Change in Left Ventricular Ejection Fraction (LVEF) from baseline to 12 months of therapy as measured by echocardiography (Echo).

Secondary Outcome Measures: Changes in left and right ventricular function, Changes in LV systolic and diastolic indexed volumes, Changes in right ventricular (RV) systolic and diastolic indexed volumes, Changes in LV sphericity index and LV end-systolic global wall stress, Changes in sleep duration and sleep stages as well as arousals, Changes in sleep-disordered breathing, Changes in quality of life assessed by Kansas City Cardiomyopathy Questionnaire (KCCQ)

Example 16

Clinical Trial for Obesity Hypoventilation Syndrome

The aim of the study is to determine the effect of an $H_2S$ donor compound in patients admitted to hospital with a sudden worsening of their existing breathing insufficiency, including an increase of carbon dioxide in the blood (hypercapnia) and acidity of the blood.

Patients admitted with acute exacerbation of chronic respiratory failure, or inpatients who suffer a deterioration in respiratory status, defined as 7.25<pH<7.35, $PaCO_2$>6.0 kPa, and respiratory rate >20 bpm are enrolled in the study and administered an IV formulation comprising the following compound:

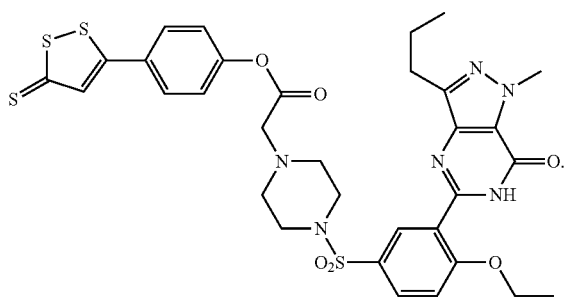 [SMILES: CCCc1nn(C)c2c(=O)[nH]c(-c3cc(S(=O)(=O)N4CCN(CC(=O)Oc5ccc(-c6cc(=S)ss6)cc5)CC4)ccc3OCC)nc12]

Primary Outcome Measures: pH of arterial blood after 1 hour of treatment with compound compared to baseline value.

Secondary Outcome Measures: pH of arterial blood after 4 hours of treatment with compound compared to baseline value, Carbon dixoide level of arterial blood after 1 hour of treatment with compound compared to baseline.

Respiratory rate after 1 hour of treatment with non-invasive ventilation compared to baseline value, Carbon dioxide level in arterial blood after 4 hours of treatment with compound compared to baseline value, Respiratory rate at 4+ hours, Respiratory rate after 4 hours of treatment with non-invasive ventilation compared to baseline value, Overnight mean transcutaneous carbon dioxide, mean overnight transcutaneous carbon dioxide during sleep period, $PaCO_2$ at 1+ hours, $PaCO_2$ at 4+ hours

Example 17

Clinical Trial for Obesity Hypoventilation Syndrome

Following the procedure in example 16, the following HO-2 inhibitor compound is tested for effect on obesity hypoventilation syndorome:

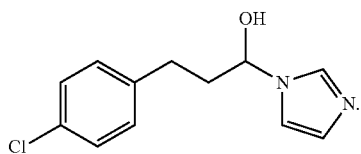 [SMILES: OC(CCc1ccc(Cl)cc1)n1ccnc1]

Example 18

Clinical Trial for Opioid Induced Sleep Apnea

The aim of the study is to determine the effect of a CSE inhibitor PAG in patients suffering from opioid induced sleep apnea. The goal of the study is to determine whether administration of PAG to patients undergoing treatment with opioids for chronic pain results in a decrease in the frequency and severity of sedation-induced respiratory arrhythmias (central and obstructive apneas). Patients will be divided into placebo and treatment groups.

Primary Outcome Measures: EEG activity will be used to directly assess CNS arousability during the changes in airway pressure via power spectral analytic measure of Alpha, Beta and Gamma frequency EEG. Epworth sleepiness score will be determined.

Secondary Outcome Measures: BIS monitor of sedation will allow the sedation state achieved in the laboratory setting to be related to clinical sedation. It will also provide a quantitative correlation of the OAA/S and the pain VAS scores.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating or reducing incidence of a central sleep apnea syndrome (CSAS) disorder in an individual diagnosed with CSAS comprising administering a therapeutically effective amount of DL-propargylglycine (PAG), beta cyano L-alanine (BCA), or combinations thereof, wherein the individual is not suffering from anatomically compromised airway patency of an obesity individual.

2. The method of claim 1, wherein the individual is suffering from a central sleep apnea syndrome (CSAS) disorder selected from the group consisting of: central sleep apnea (CSA), Cheyne-Stokes breathing-central sleep apnea (CSB-CSA), congenital central hypoventilation syndrome (CCHS), obstructive sleep apnea (OSA), idiopathic central sleep apnea (ICSA), narcotic-induced CSA, high altitude periodic breathing, chronic mountain sickness, impaired respiratory motor control associated with stroke, and impaired respiratory motor control associated with a neurologic disorder.

3. The method of claim 1, wherein the method comprises administration of PAG to the individual.

4. The method of claim 1, further comprising administration of a second agent, wherein the second agent comprises carbonic anhydrase inhibitors, cholinesterase inhibitors, adenosine inhibitors, progestational agents, opiod antagonists, central nervous system stimulants, selective serotonin reuptake inhibitors (SSRis), antidepressants, antihypertensives, calcium channel antagonists, ACE inhibitors, respiratory stimulants, alpha-2 adrenergic agonists, gamma aminobutyric acid agonists, glutamate antagonists, or combinations thereof.

5. The method of claim 1, further comprising administration of a second agent, wherein the second agent comprises acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, sabeluzole, or combinations thereof.

6. The method of claim 1, wherein the PAG or BCA is administered orally, subcutaneously, topically, intramuscularly, or intravenously.

7. A method of treating or reducing incidence of a central sleep apnea syndrome (CSAS) disorder in an individual diagnosed with CSAS comprising administering a therapeutically effective amount of an agent selected from PAG, BCA or combinations thereof, wherein the agent is administered chronically.

8. The method of claim 7, wherein the individual is suffering from a central sleep apnea syndrome (CSAS) disorder selected from the group consisting of: central sleep apnea (CSA), Cheyne-Stokes breathing-central sleep apnea (CSB-CSA), congenital central hypoventilation syndrome (CCHS), obstructive sleep apnea (OSA), idiopathic central sleep apnea (ICSA), narcotic-induced CSA, high altitude periodic breathing, chronic mountain sickness, impaired respiratory motor control associated with stroke, and impaired respiratory motor control associated with a neurologic disorder.

9. The method of claim 7, wherein the agent is PAG.

* * * * *